US011311570B2

(12) United States Patent
Vetter

(10) Patent No.: US 11,311,570 B2
(45) Date of Patent: Apr. 26, 2022

(54) METHOD OF INDUCING SATIETY

(71) Applicant: PERORA GMBH, Heidelberg (DE)

(72) Inventor: Dirk Vetter, Heidelberg (DE)

(73) Assignee: PERORA GMBH, Heidelberg (DE)

( * ) Notice: Subject to any disclaimer, the term of this patent is extended or adjusted under 35 U.S.C. 154(b) by 142 days.

(21) Appl. No.: 15/505,589

(22) PCT Filed: Aug. 11, 2015

(86) PCT No.: PCT/EP2015/068502
§ 371 (c)(1),
(2) Date: Feb. 21, 2017

(87) PCT Pub. No.: WO2016/023924
PCT Pub. Date: Feb. 18, 2016

(65) Prior Publication Data
US 2017/0258824 A1 Sep. 14, 2017

(30) Foreign Application Priority Data

Aug. 11, 2014 (EP) .................................... 14180565
Sep. 6, 2014 (EP) .................................... 14183861
Jul. 7, 2015 (EP) .................................... 15175571

(51) Int. Cl.
| | | |
|---|---|---|
| *A61K 31/78* | (2006.01) | |
| *A23L 33/00* | (2016.01) | |
| *A23L 33/15* | (2016.01) | |
| *A23L 33/17* | (2016.01) | |
| *A23L 33/21* | (2016.01) | |
| *A61K 9/00* | (2006.01) | |
| *A61K 9/16* | (2006.01) | |
| *A23L 29/20* | (2016.01) | |
| *A61K 31/20* | (2006.01) | |
| *A61K 31/717* | (2006.01) | |
| *A61K 31/745* | (2006.01) | |
| *A61K 31/79* | (2006.01) | |
| *G16H 20/10* | (2018.01) | |

(52) U.S. Cl.
CPC .............. *A61K 31/78* (2013.01); *A23L 29/20* (2016.08); *A23L 33/00* (2016.08); *A23L 33/15* (2016.08); *A23L 33/17* (2016.08); *A23L 33/21* (2016.08); *A23L 33/30* (2016.08); *A61K 9/0065* (2013.01); *A61K 9/1617* (2013.01); *A61K 9/1635* (2013.01); *A61K 9/1652* (2013.01); *A61K 31/20* (2013.01); *A61K 31/717* (2013.01); *A61K 31/745* (2013.01); *A61K 31/79* (2013.01); *A23V 2002/00* (2013.01); *G16H 20/10* (2018.01)

(58) Field of Classification Search
CPC .......... A23L 29/20; A23L 33/00; A23L 33/30; A23L 33/15; A23L 33/17; A23L 33/21; A23V 2002/00; A61K 31/78; A61K 9/1617; A61K 31/20; A61K 31/717; A61K 31/745; A61K 31/79; A61K 9/0065; A61K 9/1635; A61K 9/1652; A61K 31/197; A61K 31/215; A61K 47/30; A61K 47/36; A61P 3/04; G06F 19/324; G06F 19/3456
See application file for complete search history.

(56) References Cited

U.S. PATENT DOCUMENTS

| | | | |
|---|---|---|---|
| 4,009,265 A | | 2/1977 | Howard et al. |
| 4,483,847 A | * | 11/1984 | Augart ................ A61K 9/2013 424/470 |
| 5,104,677 A | | 4/1992 | Behr et al. |
| 5,403,593 A | | 4/1995 | Royce |
| 5,545,414 A | * | 8/1996 | Behr .................... A61K 9/0056 424/484 |
| 5,571,533 A | | 11/1996 | Santus et al. |
| 5,753,253 A | | 5/1998 | Meyer |
| 6,368,635 B1 | | 4/2002 | Akiyama et al. |
| 6,428,813 B1 | | 8/2002 | Akiyama et al. |
| 6,429,190 B1 | | 8/2002 | Portman |
| 6,835,397 B2 | | 12/2004 | Lee et al. |
| 8,246,985 B2 | | 8/2012 | Park et al. |
| 8,962,046 B2 | | 2/2015 | Malkki |

(Continued)

FOREIGN PATENT DOCUMENTS

| | | |
|---|---|---|
| CN | 1251035 | 4/2000 |
| CN | 1794921 | 6/2006 |

(Continued)

OTHER PUBLICATIONS

Sigma Aldrich, Sodium Carboxymethylcellulose product information, obtained from the web at https://www.sigmaaldrich.com/catalog/product/sigma/c5013?lang=en&region=US on Jun. 16, 2020. (Year: 2020).*

M. Vervloet, L. van Dijk, J. Santen-Reestman, B. van Vlijmen, P. van Wingerden, M.L. Bouvy, and D.H. de Bakker, "SMS reminders improve adherence to oral medication in type 2 diabetes patients who are real time electronically monitored", International Journal of Medical Informatics, 81 (2012) 594-604. (Year: 2012).*

(Continued)

*Primary Examiner* — Mina Haghighatian
*Assistant Examiner* — Nathan W Schlientz
(74) *Attorney, Agent, or Firm* — Hoxie & Associates LLC

(57) ABSTRACT

The invention provides a method of inducing satiety in a subject comprising a step of orally administering a composition comprising an effective amount of a first agent capable of inducing satiety and of a second agent capable of augmenting the satiety-inducing effect of the first agent. Also disclosed are compositions for carrying out the method, and a body weight management system comprising such compositions in combination with a device configured for the collection, storage and/or display of information relating to a subject's response to a predefined therapeutic regimen of orally administering the composition.

19 Claims, No Drawings

(56) References Cited

U.S. PATENT DOCUMENTS

| | | | |
|---|---|---|---|
| 9,457,048 | B2 | 10/2016 | Davis |
| 2002/0012733 | A1 | 1/2002 | Kester et al. |
| 2003/0008810 | A1 | 1/2003 | Portman |
| 2003/0013679 | A1 | 1/2003 | Wolf et al. |
| 2003/0161885 | A1 | 8/2003 | Beisel et al. |
| 2003/0170371 | A1 | 9/2003 | Jobe et al. |
| 2003/0203004 | A1 | 10/2003 | Kelm et al. |
| 2004/0126424 | A1 | 7/2004 | Jandacek et al. |
| 2004/0258803 | A1* | 12/2004 | Van Benthum ....... A23L 33/115 426/89 |
| 2005/0276900 | A1 | 12/2005 | Ullanoormadam |
| 2006/0073203 | A1 | 4/2006 | Ljusberg-Wahren et al. |
| 2006/0134144 | A1 | 6/2006 | Chung et al. |
| 2006/0141053 | A1 | 6/2006 | Menjoge et al. |
| 2006/0141101 | A1* | 6/2006 | Chen ................. A21D 2/18 426/99 |
| 2007/0286909 | A1 | 12/2007 | Smith et al. |
| 2008/0044481 | A1 | 2/2008 | Harel |
| 2008/0075688 | A1 | 3/2008 | Hird et al. |
| 2009/0196848 | A1* | 8/2009 | Davis .................. A61K 9/0056 424/78.31 |
| 2009/0281039 | A1* | 11/2009 | Malkki ................. A23L 33/30 514/1.1 |
| 2010/0216740 | A1 | 8/2010 | Stahl et al. |
| 2011/0027412 | A1 | 2/2011 | Spence et al. |
| 2011/0123609 | A1 | 5/2011 | Borude et al. |
| 2011/0229602 | A1 | 9/2011 | Aymard et al. |
| 2012/0052151 | A1 | 3/2012 | Sannino et al. |
| 2012/0058195 | A1 | 3/2012 | Harel |
| 2014/0234449 | A1 | 8/2014 | Nielsen et al. |
| 2015/0305394 | A1 | 10/2015 | Mazer et al. |
| 2017/0258725 | A1 | 9/2017 | Vetter |
| 2018/0027860 | A1 | 2/2018 | Halford et al. |
| 2018/0185327 | A1 | 7/2018 | Vetter |
| 2018/0200189 | A1 | 7/2018 | Vetter |
| 2018/0214382 | A1 | 8/2018 | Vetter |
| 2018/0214411 | A1 | 8/2018 | Vetter |
| 2019/0110514 | A1 | 4/2019 | Vetter |

FOREIGN PATENT DOCUMENTS

| | | | |
|---|---|---|---|
| DE | 3139920 | | 4/1983 |
| EP | 0246294 B1 * | | 9/1990 ............ A61K 9/2866 |
| EP | 0514008 A1 * | | 11/1992 ............ A61K 9/1617 |
| EP | 0580861 | | 2/1994 |
| EP | 2098222 | | 9/2009 |
| JP | H05132416 | | 5/1993 |
| JP | H05132416 A | | 5/1993 |
| JP | 2000178206 | | 6/2000 |
| JP | 2002188095 | | 7/2002 |
| JP | 2005046054 | | 2/2005 |
| WO | WO 99/38052 | | 7/1999 |
| WO | WO 2001/005408 | | 1/2001 |
| WO | WO 2001/017377 | | 3/2001 |
| WO | WO 2003/037355 | | 5/2003 |
| WO | WO 2004/060401 | | 7/2004 |
| WO | WO 2005/002430 | | 1/2005 |
| WO | WO 2007/123338 | | 11/2007 |
| WO | WO 2008/017659 | | 2/2008 |
| WO | WO 2009/07131 | | 6/2009 |
| WO | WO 2010/059725 A1 | | 5/2010 |
| WO | WO 2011/096950 | | 8/2011 |
| WO | WO 2011/136975 | | 11/2011 |
| WO | WO 2014/066680 | | 5/2014 |
| WO | WO 2014/066682 | | 5/2014 |
| WO | WO 2014/202997 | | 12/2014 |
| WO | WO 2016/014500 | | 1/2016 |
| WO | WO 2017/005887 | | 1/2017 |

OTHER PUBLICATIONS

JP2000178206, FANCL Corp, "Lubricant Containing Plant Fat and Oil," Jun. 27, 2000, English language machine translation of abstract, Espacenet, date obtained: Jun. 19, 2017, 1 page, <URL: https://worldwide.espacenet.com/publicationDetails/biblio?II=1&ND=3&adjacent=true&locale=en_EP&FT=D&date=20000627&CC=JP&NR=2000178206A&KC=A>.

JP2002188095, FANCL Corp, "Vegetable Oil and Fat Powder and Food Composition Containing the Powder," Jul. 5, 2002, English language machine translation of abstract, Espacenet, date obtained: Jun. 19, 2017, 1 page, <URL: https://worldwide.espacenet.com/publicationDetails/biblio?II=1&ND=3&adjacent=true&locale=en_EP&FT=D&date=20020705&CC=JP&NR=2002188095A&KC=A>.

International Search Report of International PCT/EP2015/068502 dated Sep. 22, 2015, 4 pages.

Carvalho et al., "Mucoadhesive drug delivery systems," Brazilian Journal of Pharmaceutical Sciences, vol. 46(1): 1-17 (2010).

Flint et al., "Reproducibility, power and validity of visual analogue scales in assessment of appetite sensations in single test meal studies," International Journal of Obesity, vol. 24: 38-48 (2000).

International Search Report for International Application No. PCT/EP2015/068502, dated Sep. 22, 2015, 4 pages.

International Search Report for International Application No. PCT/EP2016/066214, dated Oct. 11, 2016, 4 pages.

International Search Report for International Application No. PCT/EP2016/066216, dated Oct. 14, 2016, 3 pages.

International Search Report for International Application No. PCT/EP2016/066217, dated Oct. 10, 2016, 4 pages.

International Search Report for International Application No. PCT/EP2016/066218, dated Oct. 10, 2016, 4 pages.

International Search Report for International Application No. PCT/EP2016/066220, dated Oct. 10, 2016, 4 pages.

Ivarsson et al., "Comparison of in vitro methods of measuring mucoadhesion: Ellipsometry, tensile strength and rheological measurements," Colloids and Surfaces B: Biointerfaces, vol. 92: 353-359 (2012).

JP2005046054, Nippon Kayaku KK, "Diet Food and Pharmaceutical Preparation for Diet," Feb. 24, 2005, English language machine translation of abstract, Espacenet, date obtained: Jun. 13, 2018, 1 page <https://worldwide.espacenet.com/publicationDetails/biblio?II=0&ND=3&adjacent=true&locale=en_EP&FT=D&date=20050224&CC=JP&NR=2005046054A&KC=A>.

WO2001017377, Beisel Günther, "Cross-Linked Agent for Generation of a Long-Lasting Satiety Effect and Method for the Production of the Said," Mar. 15, 2001, English language machine translation of abstract, Espacenet, date obtained: Jun. 13, 2018, 2 pages <https://worldwide.espacenet.com/publicationDetails/biblio?II=0&ND=3&adjacent=true&locale=en_EP&FT=D&date=20010315&CC=WO&NR=0117377A1&KC=A1>.

CN1251035, Takeda Chemical Ind. Ltd., "Gastrointestinal mucosa-adherent pharmaceutical composition," Apr. 19, 2000, English language machine translation of abstract, Espacenet, date obtained: Mar. 27, 2019, 1 page <URL: https://worldwide.espacenet.com/publicationDetails/biblio?II=0&ND=3&adjacent=true&locale=en_EP&FT=D&date=20000419&CC=CN&NR=1251035A&KC=A>.

CN1794921, Unilever NV, "Satiety enhancing food products," Jun. 28, 2006, English language machine translation of abstract, Espacenet, date obtained: Mar. 27, 2019, 1 page <URL: https://worldwide.espacenet.com/publicationDetails/biblio?II=0&ND=3&adjacent=true&locale=en_EP&FT=D&date=20060628&CC=CN&NR=1794921A&KC=A>.

Hermsdorff, HH, et al., "Macronutrient profile affects diet-induced thermogenesis and energy intake," Arch Latinoam Nutr., 57(1): 33-42 (2007) (Abstract Only).

International Search Report for International Application No. PCT/EP2017/053713, dated Apr. 28, 2017, 5 pages.

Makarova, S.G., et al., "Long-Chain Polyunsaturated ω-3 and ω-6 Fatty Acids as Essential Nutrients in Different Periods of Childhood," Pediatric pharmacology, 10(4): 80-88 (2013) (Russian Translation Only).

"MediSafe introduces medication reminder smartwatch," Jul. 14, 2014, EMS1, date obtained: Jan. 14, 2019, 2 pages <https://www.ems1.com/ems-products/apparel-accessories/articles/1945312-MediSafe-introduces-medication-reminder-smartwatch/>.

Rowe, R.C., et al., Handbook of Pharmaceutical Excipients, 6: 685-686 (2009).

(56) References Cited

OTHER PUBLICATIONS

"Cholecystokinin," Wikipedia, retrieved from the web Jun. 13, 2019, 8 pages, URL: <https://en.wikipedia.org/wiki/Cholecystokinin>.

Feltrin, K.L., et al., "Acute oral administration of lauric acid reduces energy intake in healthy males," e-SPEN Journal, 9: e69-e75 (2014).

Alleleyn, A., et al., "Gastrointestinal Nutrient Infusion Site and Eating Behavior: Evidence for a Proximal to Distal Gradient within the Small Intestine?" Nutrients, 8 (117): 1-15 (2016).

JPH05132416, Takeda Chemical Industries Ltd., "Matrix Adherent to Mucosa of Alimentary Tract, Preparation and Coating Agent," May 28, 1993, English language machine translation of abstract, Espacenet, date obtained: May 14, 2019, 1 page <https://worldwide.espacenet.com/publicationDetails/biblio?II=0&ND=3&adjacent=true&locale=en_EP&FT=D&date=19930528&CC=JP&NR=H05132416A&KC=A>.

Sato, S., et al., "Clinical comparison of branched-chain amino acid (L-Leucine, L-Isoleucine, L-Valine) granules and oral nutrition for hepatic insufficiency in patients with decompensated liver cirrhosis (LIV-EN study)," Hepatology Research, 31: 232-240 (2005).

"Laric Acid," Wikipedia, retrieved from the web Oct. 15, 2019, 5 pages, URL: <https://en.wikipedia.org/wiki/Medium-chain_triglyceride>.

Guerin-Deremaux, et al., "The soluble fibre NUTRIOSE induces a dose-beneficial impact on satiety over time in humans," Nutrition Research, 31:665-672 (2011).

Lefranc-Millot, et al., "Impact of a Resistant Dextrin on Intestinal Ecology: How Altering the Digestive Ecosystem with NUTRIOSEO, a Soluble Fibre with Prebiotic Properties, May Be Beneficial for Health," The Journal of International Medical Research, 40:211-224 (2012).

Chapman, et al., "Effects of small-intestinal fat and carbohydrate infusions on appetite and food intake in obese and nonobese men," Original Research Communications, American Journal of Clinical Nutrition, 69:6-12 (1999).

DE 3139920, Nittner Erich, "Agent in the for of granules based on polysaccharide gums, process for the preparation thereof and use," Apr. 28, 1983, English language machine translation, Espacenet, date obtained: Sep. 25, 2020, 1 page. <https://worldwide.espacenet.com/patent/search/family/006143620/publication/DE3139920A1?q=DE3139920>.

Del Carmen, J., "Nutritionists should consider U.S. soybean meal's mineral content when differentiating between origins," USSEC, 1-3 (2019).

Guthmann, "Pellet Formulations," 4, 33-36.

Lu, et al., "Postprandial inhibition of gastric ghrelin secretion by long-chain fatty acid through GPR120 in isolated gastric ghrelin cells and mice," Am J Physiol Gastroinstest Liver Physiol., 303(3):G367-G376 (2012).

* cited by examiner

METHOD OF INDUCING SATIETY

CROSS REFERENCE TO RELATED APPLICATIONS

This application is a United States Application under 35 U.S.C. § 371 claiming benefit of PCT Application No. PCT/EP2015/068502, filed on Aug. 11, 2015, which claims priority to and the benefit of European Patent Application Nos. 14180565.5, filed on Aug. 11, 2014, 14183861.5, filed Sep. 6, 2014, and 15175571.7, filed Jul. 7, 2015, the contents of each of which are hereby incorporated by reference in their entireties.

FIELD

The present invention relates to oral compositions for the delivery of bioactive agents to the gastrointestinal tract.

BACKGROUND

In the field of oral drug delivery it is of interest to develop gastroretentive dosage forms for bioactive substances. Substances associated with bioactivity are typically synthetic compounds, so called small molecules. Often such synthetic compounds require a slow release from their dosage form after oral administration to minimise side effects and maximise efficacy. For this purpose drug substances may be incorporated in a matrix comprising lipids. Due to the hydrophobic nature of the lipidic components of such a formulation, a lipophilic or amphiphilic bioactive substance may be released more slowly into the gastrointestinal lumen as compared to a standard tablet matrix comprising highly water-soluble excipients. Due to the fact that the release from a sustained release matrix may proceed over the course of up to six or eight hours but the typical time of gastric emptying is limited to only two hours, there is a need for engineering gastroretentive properties into such a slow release formulation in order to maximise the effective time of drug delivery. Gastroretention may be achieved by rendering the formulation mucoadhesive. A gastric mucoadhesive system will bind to the mucosa of the gastric wall and prolong the residence time of the system, providing for a more extended release period. The combination of mucoadhesive properties and slow-release lipid matrix has been addressed. US 2006/0134144 details mucoadhesive compositions for solubilisation of insoluble drugs. Here, pharmaceutical compounds are formulated with monoglycerides and oil. WO03/037355 to Reckitt Benckiser Healthcare mentions polyacrylate compositions for use in protecting mucosa. In addition to the mucoadhesive polymer, such compositions comprise Vitamins and oil. EP 0580861 to Nippon Shinyaku Company claims a sustained release capsule for adhesion in the gastrointestinal tract. Hard capsules were filled with drug substance, adhesion polymer and filler polymers and liquid paraffin. U.S. Pat. No. 5,571,533 to Recordati discloses controlled-release mucoadhesive compositions for the oral administration of drug substance furosemide. In this patent, furosemide-lipid granules were coated with mucoadhesive polymers. U.S. Pat. No. 6,368,635 to Takeda Chemical Industries describes gastrointestinal mucosa-adherent matrices. High-melting triglyceride was mixed with drug substance and acryl acid polymer, and solid dosage forms were prepared with mucoadhesive properties. From recent research in the area of anti-obesity, it has emerged that triglycerides or their digestive degradation products, free fatty acids, may act as bioactive substances in their own right. For instance, it is well documented that the infusion of lauric acid or oleic acid into the duodenum by means of a feeding tube provides for strong satiety signalling. Consequently, there is a need to provide sustained release formulations of free fatty acids.

WO 2011/136975A1 describes a method and system for displaying gastric band information, and more specifically gastric band information which can support adjustment of a gastric band. The adjustment of the gastric band may be dependent on several pieces of data. Such data may include satiety state date.

Alternative non-invasive approaches for the treatment of obesity may infer satiety or the feeling of fullness or satisfaction through a variety of different ingestible compositions such as gelling systems or certain nutrient compositions.

Whereas for gastric banding, satiety state information may be of relevance to the healthcare professional to monitor efficacy of the device, for non-invasive satiety compositions it may be useful to collect and display satiety state information in order to support administration of the satiety-inducing composition and to increase compliance.

Such satiety-state information are conventionally collected as hand written documents, or typed data entry into computer spreadsheets or forms. More preferably, such satiety-state data may be collected in real-time by means of a software application running on a computer or a mobile device such as a smartphone or a wearable device.

It is an object of the present invention to provide an effective method for delivering agents capable of inducing satiety, such as fatty acids and lipids based on fatty acids, to the gastrointestinal tract. A further object is to provide means for the delivering such fatty acids and lipids to specific regions within the gastrointestinal tract, such as the stomach or the duodenum. A further object is to provide compositions, dosage forms and/or formulations which are useful for the oral delivery of fatty acids and lipids based on fatty acids. A yet further object is to provide a treatment for obesity which encourages adherence to the therapy and motivates the patient to comply with a prescribed administration regimen.

Further objects will become apparent on the basis of the following description including the examples, and the patent claims.

SUMMARY OF THE INVENTION

In a first aspect, the invention provides an oral composition comprising an effective amount of a first agent capable of inducing satiety, a second agent capable of augmenting the satiety-inducing effect of the first agent, and optionally an amino acid, a vitamin and/or a micro-nutrient. The first agent which is capable of inducing satiety may be selected from medium or long chain fatty acid compounds. The second agent may represent a polymer capable of increasing the bioavailability or the residence time of the first agent in the gastrointestinal tract.

In a further aspect, the invention provides an ingestible particle having a sieve diameter in the range from 0.05 to 3 mm, comprising a water-swellable or water-soluble polymeric component, a first lipid component, and optionally an amino acid, a vitamin and/or a micro-nutrient. The first lipid component comprises a medium or long chain fatty acid compound. The particle is further characterised in that the water-swellable or water-soluble polymeric component is embedded within, and/or coated with, the lipid component.

The first lipid component in/by which the water-swellable or water-soluble polymeric component is embedded or coated may represent the active core of the ingestible particle. The particle may further be coated with a coating layer that comprises a second lipid component and/or a hydrophilic component. Optionally, the coating layer is substantially free of the water-swellable or water-soluble polymeric component.

Alternatively, the ingestible particle may comprise an inert core, e.g. composed of an inert material, and the first lipid component in/by which the water-swellable or water-soluble polymeric component is embedded or coated may be designed as a coating covering the inert core. Moreover, the particle may further comprise a second coating layer covering the first coating. The second coating comprises a second lipid component and/or a hydrophilic component. Optionally, the second coating layer is substantially free of the water-swellable or water-soluble polymeric component.

Preferably, the first lipid component comprises at least one medium or long chain fatty acid compound with a melting range below 37° C., either per se or in the hydrated state.

In a further aspect, the invention provides compositions for oral administration which comprise the ingestible particles or which are prepared from them, such as bottle, sachets, stick packs, capsules or tablets or other dosage units.

In a yet further aspect, the invention provides the use of the particles and of the compositions based on the particles for the prevention and/or treatment of obesity, or a disease or condition associated with obesity. Moreover, the use in appetite suppression and induction of satiety is provided.

Moreover, the invention provides a method for inducing satiety in a subject; a method of treating or preventing overweight, obesity, or a disease or condition associated with overweight or obesity in a subject; and a method of controlling or reducing the body weight of a subject; which methods comprise a step of orally administering a composition comprising an effective amount of the first agent capable of inducing satiety and of the second agent capable of augmenting the satiety-inducing effect of the first agent.

The invention furthermore provides a body weight management system comprising such composition and a device configured for the collection, storage and/or display of information relating to a subject's adherence, or the effectiveness of, a predefined therapeutic regimen of orally administering the composition.

DETAILED DESCRIPTION OF THE INVENTION

In a first aspect, an oral composition comprising an effective amount of a first agent capable of inducing satiety, a second agent capable of augmenting the satiety-inducing effect of the first agent, and optionally an amino acid, a vitamin and/or a micro-nutrient. The first agent may be any compound or mixture of compounds which, after oral ingestions by a subject, triggers a signal or signalling cascade causing the subject to experience a feeling of satiety, or a reduced feeling of hunger or appetite. The second agent, on the other hand, may be any compound or mixture of compounds which, given by itself, does not induce a feeling of satiety, but when co-administered with the first agent, is capable of augmenting the satiety-inducing effect of the first agent.

The augmentation may be achieved by a direct or indirect interaction, and effected via any pharmacological, physiological, or physical means. For example, a compound or mixture of compounds may be selected as the second agent which is capable of increasing the bioavailability of the first agent which induces satiety. Alternatively, the second agent may be selected such as to prolong the gastric residence time and/or the small intestinal residence time of the first agent.

For the avoidance of doubt, it should be understood that the presence of the amino acid, the vitamin and/or the micro-nutrient in the particles according to the invention (and/or mixtures for the preparation of said particles) is optional in all embodiments, unless where explicitly stated otherwise. This means that, as used herein, listings including the amino acid, the vitamin and/or the micro-nutrient simply refer to the specific embodiments in which the optional amino acid(s), vitamin(s) and/or micro-nutrient(s) are present, while not excluding those embodiments without these optional components.

Further, the incorporation of the amino acid, the vitamin and/or the micro-nutrient into the particles of the invention are independent of each other; i.e. the particles may be free of all these components, comprise only one, two or three of the four, or they may comprise all four of them.

It should also be understood that, as used herein, the terms 'a' or 'an' or 'the' or features described in their singular form do not exclude a plurality of the respective features. Unless explicitly stated or described otherwise, expressions such as "an amino acid", "a first agent", "a vitamin", "the micro-nutrient", "the second agent" or the like are chosen solely for reasons of simplicity and are meant to encompass one or more agent(s), amino acid(s), vitamin(s), micro-nutrient(s), polymer(s) etc.; e.g. in the form of blends, or mixtures, of two or more of the respective components.

The increase in bioavailability and/or residence time of the first agent in the upper gastrointestinal tract may optionally be effected by the second agent in that the second agent increases the strength or duration of contact of the first agent to the gastrointestinal mucosa. Optionally, the bioavailability and/or residence time of the amino acid, the vitamin and/or the micro-nutrient (if present) is also increased by the second agent in the same manner. Depending on the actual compounds selected as first and second agents, respectively, this may best be accomplished by providing a composition for oral administration in which effective amounts of the first agent and the second agent are incorporated as an intimate mixture, optionally also incorporating the amino acid, the vitamin and/or the micro-nutrient (if present) in said intimate mixture.

In a preferred embodiment, the first agent is a medium or long chain fatty acid compound, as defined below, or a mixture of two or more medium or long chain fatty acid compounds. The second agent is preferably a water-swellable or water-soluble polymeric component, as described in more detail below.

In a specific embodiment, the invention provides an ingestible particle having a sieve diameter in the range from 0.05 to 3 mm, comprising a water-swellable or water-soluble polymeric component, a first lipid component, and optionally an amino acid, a vitamin and/or a micro-nutrient. The first lipid component comprises a medium or long chain fatty acid compound. The particle is further characterised in that the water-swellable or water-soluble polymeric component is embedded within, and/or coated with, the lipid component.

The inventors have found that the ingestible particles as defined herein, and in particular oral compositions comprising or prepared from a plurality of the particles, are capable of effectively inducing satiety, of suppressing the appetite, and thereby may be used to prevent or treat obesity or conditions associated with obesity; e.g. by using the ingestible particles as defined herein and/or compositions comprising or prepared from a plurality of these particles for body weight reduction. Without wishing to be bound by theory, it is currently believed that upon oral administration, the fatty acid or fatty acid ester comprised in the particle is more effectively delivered to the mucosa of the gastrointestinal tract, such as the stomach or duodenum, by virtue of the water-swellable or water-soluble polymeric component, which may be instrumental in providing a prolonged or otherwise increased interaction of the fatty acid material with target structures in the mucosa. Furthermore, the water-swellable or water-soluble polymeric component may be instrumental in providing a prolonged or otherwise increased interaction of the amino acid, the vitamin and/or the micro-nutrient (if present) with target structures in the mucosa.

Possibly, the water-swellable or water-soluble polymeric component prolongs the integrity of the particle after ingestion as compared to a lipid particle without the water-swellable or water-soluble polymeric component. Prolonged integrity of the lipid-containing particle may result in more rapid gastric emptying of the particles and therefore more rapid interaction of particle-derived fatty acids or fatty acid esters with the intestinal mucosa. Prolonged integrity of the lipid-containing particle may also result in the delivery of fatty acids or fatty-acid esters to the more distal parts of the small intestine such as the jejunum or ileum.

Possibly, the water-swellable or water-soluble polymer component increases the digestibility of a lipid component of otherwise limited digestibility such as a hard fat such as for instance tristearin. In a published rat feeding study, tristearin (Dynasan® 118, melting range 72-75° C.) was found to provide an energy content of only 3 kcal/g, corresponding to a true digestibility of stearic acid from tristearin of only 0.15 g/g independent from intake. Possibly, the water-swellable or water-soluble polymer component enhances the particle's surface wetting properties and/or facilitates water and bile acid access and subsequent emulsification and lipase-mediated hydrolysis of the lipid.

Possibly, the water-swellable or water-soluble polymeric component provides the particle with mucoadhesive properties, in particular in combination with a prolonged integrity of the particle.

As used herein, an ingestible particle is a particle which is in principle suitable for oral ingestion, or oral administration. A particle which by virtue of its composition, size and morphology would be suitable as a food component or a component of a pharmaceutical composition for oral use is an example of an ingestible particle.

The particle has a sieve diameter in the range from about 0.05 mm to about 3 mm, which means that it would normally pass through a sieve having an aperture or opening size of about 3 mm, but not through a sieve having an aperture or opening size of about 0.05 mm or less. The particle may also have a diameter in the range from about 0.1 mm to about 2.5 mm, or from about 0.1 mm to about 2 mm, such as about 0.25±0.20 mm, about 0.5±0.25 mm, about 1.0±0.25 mm, about 1.05±0.25 mm, or about 2.0±0.25 mm, respectively. Within a composition comprising a plurality of particles according to the invention, these particle sizes should be interpreted to characterise the preferred mass median sieve diameters of the ingestible particles.

The water-swellable or water-soluble polymeric component is a hydrophilic or amphiphilic polymeric material capable of swelling in an aqueous environment. The material may comprise a mucoadhesive compound or mixture of mucoadhesive compounds, or it may be capable of inducing mucoadhesiveness to the particle. If it is a mixture, it may also comprise one or more constituents which are themselves not water-swellable or mucoadhesive, as long as the mixture is water-swellable.

As used herein, swelling by water, or in an aqueous environment, typically means the volume increase of a solid body caused by an influx, or diffusion process of water accompanied by hydration, i.e. wetting and absorption of moisture.

The water-soluble polymeric component is a hydrophilic or amphiphilic polymer of a solubility in water of at least 1 mg/L.

Prolongation of particle integrity is the prolongation of time during incubation under in vivo or simulated in vivo conditions in which the majority (more than 50%) of particles do not decrease their volume or mass or melt into droplets. Particle integrity may be readily inferred by visual inspection by the naked eye or by means of a microscope or through imaging technology, including microscopic imaging, and subsequent computer-aided image processing.

Mucoadhesiveness is the capability of adhering to a mucosa, or mucosal membrane. Various conventional methods are available to determine mucoadhesiveness, such as tensile strength measurements, ellipsometry, or rheological measurements (D. Ivarsson et al., Colloids Surf B Biointerfaces, vol. 92, pages 353-359, 2012). Even though these methods may not provide absolute values for mucoadhesiveness as such, they indicate the presence and relative magnitude of mucoadhesiveness of a material.

To determine mucoadhesiveness in the context of the invention, it is preferred that a modified falling liquid film method (described among other method in Mucoadhesive drug delivery systems, Carvalho F. C. et al., Brazilian Journal of Pharmaceutical Sciences 46 (2010)) is employed. According to the method, the selected mucous membrane (e.g. from pig stomach) is placed in a petri dish together with simulated gastric fluid at a controlled temperature of 37° C. The petri dish is placed on a table undergoing a tilting movement. Both tilting movement and volume of buffer are selected so that small waves of buffer continuously run over the surface of the mucous tissue. In the falling liquid film method, a similar agitation is achieved by pumping buffer over mucosal tissue tilted at a 450 angle. The amount of particles remaining on the mucous membrane after a specified time interval can be quantified by various methods. For instance, particles can be counted, optionally using a magnifying glass or microscope, or they may be collected, dried and measured gravimetrically.

In the context of the invention, the water-swellable or water-soluble polymeric component may have, or induce, sufficient mucoadhesive strength to cause attachment to a mucosal membrane upon contact with, and to cause the particle or a component thereof to stay attached for a period of time which is significantly longer than a material which is not mucoadhesive, such as a solid triglyceride or a lipophilic polymer, e.g. polytetrafluoroethylene. In one preferred embodiment, the water-swellable or water-soluble polymeric component comprises a mucoadhesive polymer. In particular, it may comprise at least one polymeric material selected from poly(carboxylates), chitosan, cellulose ethers, and xanthan gum.

In a further preferred embodiment, the water-swellable or water-soluble polymeric component is a plant fibre. In the context of the invention, a plant fibre includes selected individual components of plant fibres or derived therefrom, as well as their mixtures. For example, a suitable water-swellable or water-soluble polymeric component is psyllium seed husk, or psyllium seed husk fibres, also referred to as psyllium husk or simply psyllium. Psyllium seed husk are the seed coats of the seeds of Plantago ovata, also known as Desert Indianwheat or Blond Psyllium. A major component of psyllium seed husk is soluble but indigestible polysaccharide fibers which are highly swellable in water. *Psyllium* is known as a source of dietary fibre and as a mild laxative or stool softener.

If a poly(carboxylate) is used, this is preferably selected from poly(acrylic acid), poly(methacrylic acid), copolymers of acrylic and methacrylic acid, and poly(hydroxyethyl methacrylic acid). The cellulose ether is preferably selected from hydroxyethyl cellulose, hydroxypropyl cellulose (also known as hyprolose), hydroxypropyl methylcellulose (also known as hypromellose), and methylcellulose. If an ionic polymer is used such as a poly(carboxylate) and/or a carboxymethylcellulose, this may be partially or entirely neutralised, preferably as sodium or potassium salt, most preferably as the sodium salt. Moreover, the polymeric material may be at least partially crosslinked.

In a further preferred embodiment, the mucoadhesive polymer is a copolymer of acrylic acid and methacrylic acid, or of acrylic or methacrylic acid and maleic acid. The copolymer may be crosslinked with small amounts of a polyalkenyl polyether. Such copolymers are highly hydrophilic and capable of absorbing large amounts of water which causes their swelling.

Particularly suitable for carrying out the invention are, for example, carbomers. Carbomers resins are high molecular weight, crosslinked acrylic acid-based polymers. Commercial versions of carbomers are sold as e.g. Carbopol®, Noveon®, Pemulen®, Polygel®, Synthalen®, Acritamer®, or Tego Carbomer®. Most of these brands include various carbomer grades.

For example, the Carbopol® polymer series encompasses homopolymers, copolymers, interpolymers as exemplified by Carbopol® Aqua SF-1 (acrylate copolymer, a lightly cross-linked acrylate copolymer), Carbopol® Aqua SF-2 (acrylate crosspolymer-4), Carbopol® Aqua CC (polyacrylate-1 crosspolymer), Carbopol® 934 (carbomer, acrylate homopolymer cross-linked with allyl ethers of sucrose), Carbopol® 940 (carbomer), Carbopol® 941 (carbomer), Carbopol® 971P (carbomer, lightly crosslinked with allyl pentaerythritol), Carbopol® 71G (a free-flowing granular form of Carbopol® 971P for use in direct compression formulations), Carbopol® 974P (carbomer, highly crosslinked), Carbopol® 980 (carbomer), Carbopol® 980 (carbomer), Carbopol® 981 (carbomer, allyl pentaerythritol crosslinked), Carbopol® 1342 (acrylates/C 10-30 alkyl acrylate crosspolymer, copolymer of acrylic acid and C10-C30 alkyl acrylate crosslinked with allyl pentaerythritol), Carbopol® 1382 (acrylates/C10-30 alkyl acrylate crosspolymer, copolymer of acrylic acid and C10-C30 alkyl acrylate crosslinked with allyl pentaerythritol), Carbopol® 2984 (carbomer), Carbopol® 5984 (carbomer), Carbopol® Ultrez 10 (carbomer), Carbopol® Ultrez 20 (acrylates/C10-30 alkyl acrylate crosspolymer), Carbopol® Ultrez 21 (acrylates/C10-30 alkyl acrylate crosspolymer), Carbopol® Ultrez 30 (carbomer), Carbopol® ETD 2001, Carbopol® ETD 2020 (acrylates/C10-30 alkyl acrylate crosspolymer, interpolymer containing a block copolymer of polyethylene glycol and a long chain alkyl acid ester), Carbopol® ETD 2050 (carbomer).

Polymer grades approved for pharmaceutical use are preferred among these, such as those which comply with a pharmacopoeial monograph, such as the monograph "Carbomer" of the European Pharmacopoeia (Ph. Eur. 8) or the monographs in the US Pharmacopoeia/National Formulary (USP-NF) with the titles, "Carbomer 910", "Carbomer 934", "Carbomer 934P", "Carbomer 940", "Carbomer 941", "Carbomer Homopolymer", "Carbomer Copolymer", "Carbomer Interpolymer", or "Carbomer 1342".

Also particularly suitable are polycarbophils (USP-NF), which represent high molecular weight acrylic acid polymers crosslinked with divinyl glycol. They provide excellent bioadhesive properties. An example of a preferred grade of polycarbophil is NOVEON® AA-1.

Optionally, the water-swellable or water-soluble polymeric component comprises at least one polysaccharide approved for oral use as excipient or food additive or food ingredient. The at least one polysaccharide may be selected from the groups of cationic polysaccharides, anionic polysaccharides and non-ionic polysaccharides.

Suitable cationic polysaccharides include, but are not limited to, chitosan, polysaccharides modified by means of quaternary ammonium groups (for example cationic guar gum, cationic cellulose, cationic hydroxyethyl cellulose, and cationic starch), derivatives thereof, or mixtures of two or more thereof.

Alternatively, the cationic polysaccharide is a polymeric material with basic amino groups which are at least partially protonated in a neutral environment. The cationic polysaccharide may be provided or incorporated as a free base, as a quantitatively protonated salt form, or any mixture of the two forms.

The "free base" form refers to a polymer such as polyglucosamine (chitosan) comprising amino side chains in the base form, e.g. —$NH_2$. The "salt form" refers to a polymer such as polyglucosamine (chitosan) comprising amino side chains in the salt form, e.g. —$NH_3^-Cl^-$ for chloride salts of ammonium groups. It is understood that the salt form may refer to mixtures of salts, e.g. the salt form may be composed of mixtures of different salts such as —$NH_3^+Cl^-$ and —$NH_3^+CH_3$—$COO^-$. "Any mixture of the two forms" refers to a polymeric material comprising amino groups, where a fraction of the amino groups is present in the free base form, e.g. as —$NH_2$ for primary amino groups, and a fraction of those side chains is present in the salt form, e.g. —$NH_3^+Cl^-$. For instance, such a mixture may be referred to as partial chloride salt of chitosan.

"Chitosan" for the purpose of the invention is defined as chitosan derived from fungi or derived by deacetylation of chitin, wherein the average degree of deacetylation is preferably more than about 75%, more than about 80%, more than about 90%, or more than about 95%, respectively. The degree of deacetylation refers to the percentage of the chitin's amino groups that are deacetylated. A particularly preferred chitosan is derived from fungal biomass selected from the group consisting of *Candida Guillermondii, Aspergillus niger, Aspergillus terreus*, and combinations thereof, the chitosan containing material having greater than 85 percent deacetylation of N-acetyl groups in the chitin and exhibiting a viscosity of less than 25 centipoise (mPa's) at 25° C. in 1 percent aqueous acetic acid.

Suitable anionic polysaccharides include, but are not limited to, sulphated glycosamino glycans including heparans, heparansulfates, heparins; alginates; propylene glycol alginates; carrageenans; cellulose sulfate; carboxymethyl cellulose; fucoidan; galactans containing glucuronic acid or galacturonic acid; chondroitins or chondroitin sulphates; gellan gums; hyaluronans and hyaluronic acids; modified starches such as octenyl succinate starches or monostarch phosphates, oxidised starches or carboxymethylated starches; pectic acids, pectins including amidated pectins, homogalacturonans, substituted galacturonans, rhamnogalacturonans, their methyl and ethyl esters; porphyrans; sulphated galactanes; tragacanth or gum karaya; xanthan gums and xylans.

One particularly suitable polycarboxylate polysaccharide is alginic acid. Alginic acid is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

The anionic polysaccharide may be incorporated in the form of a free acid, or as the neutralised salt form of the acid, or as a mixture of these, i.e. as a partially neutralised salt. The "free acid" form refers to a polymeric material comprising acid groups in the non-ionised, protonated acid form, e.g. —COOH or —$SO_4H_2$. The "salt form" refers to a polymeric material with acid groups in the ionised form, or salt form, e.g. —COO$^-$Na$^+$ for sodium salts of carboxylates or —$SO_4^{2-}$2Na$^+$ for sodium salts of sulphates. It is understood that the salt form may refer to mixtures of salts, e.g. the salt form may be composed of mixtures of —COO$^-$Na$^+$ and —COO$^-$K$^+$ or —COO—Ca$^{2+}$—COO— salts. "Any mixture of the two forms" refers to a polymeric material comprising acid groups, where a fraction of those groups is present in the non-ionised acid form, e.g. as —COOH for carboxylic acids, and another fraction of the acid groups is present in the ionised salt form, e.g. —COO$^-$Na$^+$ for sodium salts of carboxylic acids. For instance, such a mixture may be referred to as partial sodium salt of alginic acid.

Preferably, the anionic polysaccharide is an anionic dietary fibre. Dietary fibres, for the purpose of the invention, are carbohydrate polymers with ten or more monomeric units which are not hydrolysable by endogenous enzymes in the small intestine of humans. They typically represent carbohydrate polymers which have been obtained from food raw material by physical, enzymatic or chemical means, or synthetic carbohydrate polymers.

Preferably, the anionic polysaccharide is alginic acid, carboxymethylcellulose, hyaluronan, sodium alginate, propylene glycol alginate, carrageenan, gellan gum, pectin, tragacanth or xanthan gum. Particularly preferred is that the at least one anionic polysaccharide is carboxymethylcellulose, sodium alginate or propylene glycol alginate, pectin, xanthan gum, or hyaluronan. Optionally, a combination of anionic polysaccharides is employed, such as sodium alginate and xanthan, or sodium alginate and pectin.

Pectic polysaccharides (pectins) are rich in galacturonic acid. Several distinct polysaccharides have been identified and characterised within the pectic group. Homogalacturonans are linear chains of α-(1-4)-linked D-galacturonic acid. Substituted galacturonans are characterised by the presence of saccharide appendant residues (such as D-xylose or D-apiose in the respective cases of xylogalacturonan and apiogalacturonan) branching from a backbone of D-galacturonic acid residues. Rhamnogalacturonan I pectins (RG-I) contain a backbone of the repeating disaccharide: 4)-α-D-galacturonic acid-(1,2)-α-L-rhamnose-(1). From many of the rhamnose residues, sidechains of various neutral sugars may branch off. The neutral sugars are mainly D-galactose, L-arabinose and D-xylose, with the types and proportions of neutral sugars varying with the origin of pectin. Another structural type of pectin is rhamnogalacturonan II (RG-II).

Isolated pectin has a molecular weight of typically 60-130, 000 g/mol, varying with origin and extraction conditions. In nature, around 80 percent of carboxyl groups of galacturonic acid are esterified with methanol. This proportion is decreased to a varying degree during pectin extraction. The ratio of esterified to non-esterified galacturonic acid determines the behaviour of pectin in food applications. This is why pectins are classified as high-vs. low-ester pectins (short HM vs. LM-pectins), with more or less than half of all the galacturonic acid esterified. The non-esterified galacturonic acid units can be either free acids (carboxyl groups) or salts with sodium, potassium, or calcium. The salts of partially esterified pectins are called pectinates; if the degree of esterification is below 5 percent the salts are called pectates; the insoluble acid form pectic acid. Amidated pectin is a modified form of pectin. Here, some of the galacturonic acid is converted with ammonia to carboxylic acid amide. Most preferred pectins are high ester pectins.

Suitable non-ionic polysaccharides include, but are not limited to, agaroses; amylopectins; amyloses; arabinoxylans; beta glucans including callose, curdlan, chrysolaminarin or leucosin, laminarin, lentinan, lichenin, pleuran, schizophyllan, zymosan; capsulans; celluloses including hemicelluloses, cellulose esters such as cellulose acetate, cellulose triacetate, cellulose propionate, cellulose acetate propionate and cellulose acetate butyrate; cellulose ethers such as methylcellulose, hydroxyethyl methylcellulose, hydroxypropyl methylcellulose (hypromellose), hydroxyethyl cellulose, hydroxypropyl cellulose (hyprolose), hydroxyethyl hydroxypropyl cellulose, methyl ethyl cellulose or alkoxy hydroxyethyl hydroxypropyl cellulose, wherein the alkoxy group is unbranched or branched and comprises 2 to 8 carbon atoms; chitins; cyclodextrins; dextrans; dextrins (for example commercially available as Nutriose® or Benefiber®); galactoglucomannans; galactomannans including fenugreek gum, guar gum, tara gum, locust bean gum or carob gum; glucomannans including konjac gum; fructans including inulin, levan, sinistrin or phlein; maltodextrins; glycogens; pullulans; starches including resistant starches, modified starches such as acetylated starch, hydroxypropylated starch or hydroxyethyl starch; polydextroses; welan gum and xyloglycans.

Preferably, the non-ionic polysaccharide is a non-ionic dietary fibre. Preferably, the non-ionic polysaccharide is selected from the group consisting of beta glucans, cellulose ethers, guar gums, galactomannans, glucomannans, inulins and dextrins. Preferably, the non-ionic polysaccharide is hydroxypropyl methylcellulose (hypromellose) or locust bean gum, or oat or barley beta glucan or konjac gum or resistant dextrin. Among the particularly preferred non-ionic polysaccharides are hydroxypropyl methylcellulose (hypromellose), hydroxypropylcellulose, beta glucan from oat or barley and resistant dextrin from starch.

Resistant dextrins are short chain glucose polymers without sweet taste which are relatively resistant to the hydrolytic action of human digestive enzymes. They can be made for instance from wheat (NUTRIOSE® FB range or Benefiber®) or maize starch (NUTRIOSE® FM range), using a highly controlled process of dextrinisation followed by a chromatographic fractionation step. During the dextrinisation step, the starch undergoes a degree of hydrolysis followed by repolymerisation that converts it into fibre: in addition to the typical starch α-1,4 and α-1,6 digestible linkages, non-digestible glycosidic bonds such as β-1,2 or β-1,3, are formed, which cannot be cleaved by enzymes in the digestive tract.

Optionally, the water-swellable or water soluble polymeric component according to the invention comprises more than one polysaccharide. Preferred is in particular the selection of an anionic polysaccharide and a non-ionic polysaccharide, especially the combination of xanthan gum and hydroxypropyl methylcellulose (hypromellose).

Optionally, the water-swellable or water soluble polymeric component according to the invention comprises a synthetic water swellable or water soluble polymeric material such as polyvinyl alcohol, polyvinyl acetate, polyethylene glycols (PEG), polypropylene glycols (PPG) or polyvinylpyrrolidones (PVP). Such polymer may be linear, branched or crosslinked, as for instance in crospovidone (crosslinked polyvinylpyrrolidone), or a PEG hydrogel.

Optionally, the water-swellable or water-soluble polymeric component comprises a thiolated polymer such as chitosan-4-thiobutylamidine, a chitosan-thioglycolic acid conjugate, a chitosan-cysteine conjugate, a chitosan glutathione conjugate, a polycarbophil-cysteine conjugate, a polyacrylic acid-cysteine conjugate, a carboxymethyl cellulose-cysteine conjugate, or any mixture or combination of two or more of these.

The first lipid component comprises a medium or long chain fatty acid compound. A fatty acid compound, as used herein, may refer to a free fatty acid, a partially or completely neutralised fatty acid, i.e. the salt of a fatty acid, such as a sodium, potassium or calcium salt, or an esterified fatty acid. An esterified fatty acid may have, as alcohol residue, a glycerol, so that the esterified fatty acid is a mono-, di- or triglyceride. The acyl chain of the fatty acid may be saturated or unsaturated.

A medium chain fatty acid is understood as fatty acid with an acyl residue of 6 to 12 carbon atoms, whereas a long chain fatty acid means a fatty acid with an acyl chain of 13 to 21 carbon atoms. Among the preferred medium chain fatty acids are caprylic acid, capric acid, and lauric acid, including their esters and salts, in particular their mono-, di- and triglycerides and their sodium, potassium and calcium salts. In the case of di- and triglycerides, these may also have different fatty acid residues per glyceride molecule. Examples of preferred long chain fatty acids include myristic acid, palmitic acid, stearic acid, arachidic acid, behenic acid, myristoleic acid, palmitoleic acid, sapienic acid, oleic acid, linoleic acid, and linolenic acid, and the respective salts and glycerides.

In one of the preferred embodiments, the first lipid component comprises one or more partial glycerides of a medium or long chain fatty acid, in particular monoglycerides of a medium or long chain fatty acid. For example, monoolein or monolaurin are very suitable for carrying out the invention, individually or in combination with each other. As used herein, a monoglyceride such as monoolein or monolaurin may be incorporated as a substantially pure compound or as a mixture of mono- and diglycerides or even mono-, di- and triglycerides with various fatty acids, but with a high content ("enriched") of a particular monoglyceride compound. For example, a monoolein grade may be used which comprises at least about 40% (or at least about 50%, or 60% or 70% or 80% or 90%) of the actual monoglyceride of oleic acid.

The first lipid component may of course represent a mixture incorporating two or more fatty acids, and/or fatty acid esters or salts. For example, the component may comprise one or more a fatty acids, which may be partially or completely neutralised, in combination with one or more glycerides, such as triglycerides.

The constituent(s) of the first lipid component may represent a native, synthetic or semisynthetic material. For example, cocoa butter may be used, which is itself a mixture of various lipid compounds, most of which represent fatty acid compounds as defined herein. Another preferred constituent of the first lipid component is palm stearin or palm kernel stearin. Palm stearin is the solid fraction of palm oil that is produced by partial crystallization at controlled temperature.

In one embodiment, the first lipid component comprises one or more free fatty acids. For example free oleic acid or lauric acid may be part of the lipid component. Other preferred free fatty acids are mixtures of unsaturated fatty acids such as the so-called omega fatty acids or conjugated linoleic acids. Conjugated linoleic acids (CLA) are a family of isomers of linoleic acid. Conjugated linoleic acid is both a trans fatty acid and a cis fatty acid as the double bonds of CLAs are conjugated and separated by a single bond between them. Brands of CLAs are marketed as dietary supplements (Tonalin®, BASF, and Clarinol®, Stepan). Omega-3 fatty acids are polyunsaturated fatty acids (PUFAs) with a double bond ($C=C$) at the third carbon atom from the end of the carbon chain. Examples of omega-3 fatty acids are α-linolenic acid (ALA) (found in plant oils), eicosapentaenoic acid (EPA), and docosahexaenoic acid (DHA) (both commonly found in marine oils). If the first lipid component comprises an unsaturated fatty acid, it may also comprise an antioxidant such as vitamin E or a derivative thereof.

In one of the preferred embodiments, the medium or long chain fatty acid compound in the first lipid component, either per se in vitro or in the hydrated state in vivo, has a melting range of below 37° C. As used herein, the melting range is understood as being below 37° C. if the lower (but not necessarily the upper) limit of the range is below 37° C. In other words, a compound having a melting range of 35° C. to 38° C. is an example of a material with a melting range of below 37° C. according to the invention. In other words, at least some of the fatty acid material in the lipid component should melt at the physiological temperature of the human body according to this embodiment. Moreover, the specified melting range is also met if the lipid component is capable of hydration, wherein the melting range in the hydrated state is below 37° C. Such behaviour of some lipids has also been described as "melting by hydration".

According to a further preference, the first lipid component comprises a medium or long chain fatty acid compound having a melting range, or lower limit of the melting range, between about 10° C. and 37° C., or between about 25° C. and 37° C., respectively.

It has been surprisingly found by the inventors that particles containing the water-swellable or water-soluble polymeric component embedded in, or coated with, a lipid component comprising such low-melting fatty acid compound(s) are capable of exhibiting a prolonged integrity of the particles. Possibly, mucoadhesive properties are inferred to the particles, depending on the nature of the polymeric component. Possibly, these effects alone or in combination also contribute to, or are related to, the prolonged gastric residence time of the particles, the increased bioavailability of the lipid(s) and the induction of satiety caused by the particles' administration.

It has further surprisingly been found by the inventors that particles containing the water-swellable or water-soluble polymeric component embedded in, or coated with, a lipid component comprising such low-melting fatty acid compound(s) is capable of forming a viscous emulsion in the gastrointestinal tract. Possibly, this effect also contributes, or is related to, the prolonged gastric residence time of the particles and the induction of satiety caused by their administration.

Optionally, the first lipid component may comprise one or more further constituents which may have entirely different melting ranges. For example, a mixture of oleic acid, which has a melting range of 13° C. to 14° C., and a hard fat (i.e. a mixture of triglycerides) having a melting range of 42° C. to 45° C. may be used as the first lipid component. As an alternative to the hard fat, myristic acid (mp 54° C. to 55° C.) or lauric acid (mp 43° C. to 44° C.) may be used in such mixture. It may also be advantageous to combine a fatty acid with the salt of a fatty acid at a selected ratio such as to adjust the melting range to a desired optimum.

In one of the preferred embodiments, the fatty acid compound in the first lipid component, either per se in vitro or in the hydrated state in vivo, has a melting range of above 37° C. As used herein, the melting range is understood as being above 37° C. if the lower limit of the range is above 37° C. In other words, a compound having a melting range of 40° C. to 44° C. is an example of a material with a melting range of above 37° C. according to the invention. Moreover, the specified melting range is also met if the lipid component is capable of hydration, wherein the melting range in the hydrated state is still above 37° C. A particularly preferred first lipid component having a melting range of above 37° C. is fractionated but non-hydrogenated palm stearin or palm kernel stearin. Palm stearin is the solid fraction of palm oil that is produced by partial crystallization at controlled temperature. An example of a preferred commercial quality is Prifex® 300 from Sime Darby Unimills.

According to the invention, the water-swellable or water-soluble polymeric component is embedded within, and/or coated with, the lipid component. As used herein, the term 'embedded' means that the water-swellable or water-soluble polymeric component is largely dispersed within the lipid component, whether molecularly, colloidally or in the form of a solid suspension. The lipid component forms a continuous phase in which the water-swellable or water-soluble polymeric component is discontinuous and in dispersed form. For the avoidance of doubt, this does not exclude that some of the material representing the water-swellable or water-soluble polymeric component—typically a small fraction—is not fully embedded, but positioned at the outer surface of the lipid component.

Typically, 'embedded' also means in the context of the invention that the lipid component and the water-swellable or water-soluble polymeric component are mixed so intimately that the porosity of the resulting lipid-polymer composition is greatly reduced as compared to the particles formed from the water-swellable or water-soluble polymer itself, for instance as formed by roller compaction or agglomeration. Particle porosity may be determined by porosimetry, an analytical technique used to determine various quantifiable aspects of a material's porous nature, such as pore diameter, total pore volume, and surface area. The technique involves the intrusion of a non-wetting liquid at high pressure into a material through the use of a porosimeter.

The term 'coated' means that a particle comprising the water-swellable or water-soluble polymeric material is substantially surrounded with a layer of the lipid material representing the first lipid component. In practice, both forms ('embedded in' or 'coated with') may co-exist to some degree, depending on the method of preparation.

In one of the preferred embodiments, the particle of the invention may be designed to exhibit an active core and a coating covering the core, wherein the active core comprises the first lipid component with the embedded or coated water-swellable or water soluble polymeric component, whereas the coating comprises a second lipid component and/or a hydrophilic component. The coating may be substantially free of the water-swellable or water-soluble polymeric component.

This embodiment is particularly useful in that the coating allows for convenient oral administration without the water-swellable or water-soluble polymeric component interacting with the mucosa of the mouth or oesophagus during ingestion, as the coating acts as a protective layer. The coating also provides protection against agglomeration and sintering during manufacture, storage and shipping, and contributes to achieving an acceptable shelf life.

In other words, in this group of embodiments, the active core may be coated with a physiologically inactive coating, such as a polymeric film coating or a lipid coating. The polymeric film coating, which is based on a hydrophilic component, may be free of lipid, or it may comprise some relatively small amount of lipid e.g. as a plasticiser. The lipid coating may be solely composed of the second lipid component, or it may contain some amount of the hydrophilic component, e.g. as a disintegration enhancer.

The coating may be designed to be rapidly disintegrating so that the active core of the particle is released rapidly after swallowing. Preferably, the second lipid component, i.e. that which is incorporated in the coating of the particle, comprises one or more lipids having a melting point or melting range below about 37° C., as defined above, such as a melting range between about 25° C. and about 37° C. The composition of the second lipid component may optionally be the same as that of the first lipid component. Alternatively, it may be different.

As said, the coating of the particle according to this embodiment may comprise a hydrophilic component. This hydrophilic material may be embedded or dispersed within the second lipid material and may act as a disintegration enhancer for the coating layer. Disintegration enhancement may be achieved by various mechanisms, depending on the choice of the hydrophilic component. For example, a disintegrant—such as e.g. crospovidone, croscarmellose, low-substituted hypromellose or even ion-exchange resins may rapidly take up water, expand in volume and thereby cause the disruption of the coating. Non-swelling, highly water-soluble excipients such as sugars or sugar alcohols, on the other hand, may predominantly act as pore formers by which water channels are rapidly created by which disintegration is also enhanced. Optionally, the hydrophilic component comprises a mixture of hydrophilic compounds. Preferably, the hydrophilic component is different from the water-swellable or water soluble polymeric component and has no or only a low degree of mucoadhesiveness.

If the coating only contains the hydrophilic component but no lipid component, the hydrophilic component preferably represents a film-forming agent such as a water soluble polymer. Examples of potentially suitable film-forming polymers include methylcellulose, hyprolose, hypromellose, polyvinyl alcohol, povidone, polyvinyl acetate, (meth)acrylate copolymer, and the like. Optionally, the composition may comprise further ingredients such as one or more plasticisers, pH-modifying agents, pore formers, colouring agents, sweetening agents, flavours, anti-tack agents, or dispersion aids.

In this group of embodiments, where the particle of the invention exhibits an active core comprising the first lipid component with the embedded or coated water-swellable or water-soluble polymeric component and surrounded by a coating, it is furthermore preferred that the active core contributes at least about 50% to the weight of the total particle. Optionally, the weight of the active core is at least about 60%, or even at least about 70% of the total particle's weight.

In a related embodiment, the particle according to the invention comprises an inert core, a first coating covering the inert core, and a second coating covering the first coating. In this case, the first coating comprises the water-swellable or water-soluble polymeric component and the first lipid component, the second coating comprises a second lipid component and optionally a hydrophilic component, and the second coating is also substantially free of the water-swellable or water-soluble polymeric component. The hydrophilic component may be selected as described above. As in the previously discussed embodiment, the first lipid component with the embedded or coated water-swellable or water soluble polymeric component is surrounded with a coating layer comprising the second lipid component. The difference is that the first lipid component and the water-swellable or water soluble polymeric component do not form the core of the particle, but a layer on an inert core having a different composition.

The inert core may be composed of a pharmacologically inert material such as sucrose, starch or microcrystalline cellulose. Specific examples of suitable inert cores include spheroids with average diameters in the range of about 100 or 200 µm based on microcrystalline cellulose which are e.g. commercially available as Cellets® 100 or Cellets® 200; nonpareils of starch and sugar of similar diameter; or sugar crystals of similar diameter, e.g. as obtainable by sieving.

With respect to the composition and further optional features of the lipid components, the water-swellable or water-soluble polymeric component and the hydrophilic component, reference is made to the discussion above.

In the context of this embodiment, the inert core should preferably not contribute more than about 70% to the weight of the total particle. More preferably, the weight of the core is not higher than about 60%, or not higher than about 50% of the total particle weight. In other embodiments, the weight of the core is from about 10% to about 50%, or from about 10% to about 40%, or from about 15% to about 35% of the total particle weight.

As already discussed, it is a key feature of the invention that the water-swellable or water-soluble polymeric component is embedded within, or coated by, the first lipid component, which appears to effect an improved and/or prolonged interaction of the fatty acid with its target at the gastrointestinal mucosa. A target structure may, for example, be represented by G-protein coupled receptors (GPCRs) involved in the sensing of intestinal lipids such as GPR120.

In some embodiments, this may also result in an increased bioavailability of the first lipid component. It may also result in an increased bioavailability of the amino acid, the vitamin and/or the micro-nutrient if present. In this context, bioavailability should be broadly understood such as to include the availability of e.g. the first lipid component, or the biologically active constituents thereof, at a biological target site, such as the gastric or intestinal mucosa, in terms of the extent and/or duration of availability.

Optionally, the particle may further contain an amino acid, a vitamin, a micro-nutrient, or any combinations of these.

As used herein, an amino acid is an organic compound having an amino group and a carboxyl group, mostly in the generic structure of $NH_2$—CHR—COOH wherein R represents the side chain which is specific to each amino acid. Optionally, the carboxylic group is partially or fully neutralised. The amino acid may be provided in its L-form, its D-form or in its racemic form. In a preferred embodiment, the amino acid is a proteogenic amino acid, i.e. an amino acid which is a potential precursor of a protein in that it may be incorporated into a protein during its translation, or biosynthesis. Proteogenic L-amino acids as currently identified are L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, L-selenocysteine, L-pyrrolysine, and N-formyl-L-methionine. In another embodiment, the amino acid is selected from the 20 amino acids which form the genetic code, which group consists of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

In another preferred embodiment, the amino acid is selected from the group of the so-called essential amino acids which consists of those amino acids which the human organism cannot synthesise, i.e. L-histidine, L-isoleucine, L-leucine, L-lysine, L-methionine, L-phenylalanine, L-threonine, L-tryptophan, and L-valine.

In a further preferred embodiment, the amino acid is selected from the group consisting of L-isoleucine, L-valine, L-tyrosine, L-methionine, L-lysine, L-arginine, L-cysteine, L-phenylalanine, L-glutamate, L-glutamine, L-leucine, and L-tryptophan. From these, the group consisting of L-phenylalanine, L-leucine, L-glutamine, L-glutamate, and L-tryptophan is particularly preferred. In another preferred embodiment, the amino acid is L-tryptophan.

Optionally, the particle comprises two or more amino acids. Such mixture or combination of amino acids should preferably comprise at least one amino acid as described above, i.e. a proteogenic amino acid, or an amino acid from the group of amino acids forming the genetic code, or from the essential amino acids, or the group of amino acids consisting of L-isoleucine, L-valine, L-tyrosine, L-methionine, L-lysine, L-arginine, L-cysteine, L-phenylalanine, L-glutamate, L-glutamine, L-leucine, and L-tryptophan. Particularly preferred particles with mixtures or combinations of amino acids comprise at least one amino acid from the group consisting of L-phenylalanine, L-leucine, L-glutamine, L-glutamate, and L-tryptophan. In particular, L-tryptophan is a preferred constituent of a combination of two or more amino acids.

Also preferred are mixtures or combinations of amino acids in which at least two amino acids are members of one of the preferred groups as previously defined. Moreover, mixtures or combinations of amino acids may be used in the particles of the invention in which essentially all incorporated amino acids are members of one of the preferred groups as previously defined.

As used herein, vitamins are vital nutrients required in small amounts, which e.g. humans (or other organisms) typically cannot synthesise in sufficient quantities and which therefore must be taken up with the diet. The term 'vitamin' is conditional in that it depends on the particular organism; for instance ascorbic acid is a vitamin for humans, while many other animals can synthesise it. Vitamins are organic compounds classified by their biological and chemical activity, not by their structure. Each vitamin refers to a number of vitamers, all having the biological activity of the particular vitamin, convertible to the active form of the vitamin in the body, and grouped together under alphabetised generic descriptors, such as 'vitamin A'. Universally recognised vitamins are preferred for the present invention (related vitamers(s) in brackets): vitamin A (retinol, retinal, and the carotenoids, including beta carotene, cryptoxanthin, lutein, lycopene, zeaxanthin), vitamin B1 (thiamine), vitamin B2 (riboflavin), vitamin B3 (niacin, niacinamide), vitamin B5 (pantothenic acid), vitamin B6 (pyridoxine, pyridoxamine, pyridoxal), vitamin B7 (biotin), vitamin B8 (ergadenylic acid), vitamin B9 (folic acid, folinic acid), vitamin B12 (cyanocobalamin, hydroxycobalamin, methylcobalamin), vitamin C (ascorbic acid), vitamin D (cholecalciferol (D3), ergocalciferol (D2)), vitamin E (tocopherols, tocotrienols), vitamin K (phylloquinone, menaquinones). The vitamins according to the invention may be provided as semisynthetic and synthetic-source supplements and/or as supplements of natural origin; such as in the form of plant extracts.

As used herein, the term 'micro-nutrients' refers to nutrients required by humans and/or other organisms in small quantities for a variety of their physiological functions, their proper growth and development; including, for instance, dietary micro-minerals or trace elements in amounts generally less than 100 mg/day (as opposed to macro-minerals). The micro-minerals or trace elements include at least boron, cobalt, chromium, calcium, copper, fluoride, iodine, iron, magnesium, manganese, molybdenum, selenium, zinc. Micronutrients also include phytochemicals, such as terpenoids or polyphenolic compounds, as well as vitamins (i.e. some compounds may qualify for both categories, vitamins and micro-nutrients).

Preferred micro-nutrients according to the invention may be selected from organic acids, such as acetic acid, citric acid, lactic acid, malic acid, choline and taurine; and trace minerals such as salts of boron, cobalt, chromium, calcium, copper, fluoride, iodine, iron, magnesium, manganese, molybdenum, selenium, zinc, sodium, potassium, phosphorus, or chloride; and cholesterol.

The optional components, i.e. the amino acid, the vitamin and/or the micro-nutrient may be incorporated within the particles of the invention in different ways. For example, hydrophilic compounds such as amino acids, water-soluble vitamins and water-soluble micro-nutrients may be incorporated in admixture with the water-soluble or water-swellable polymer, whereas lipophilic compounds may be incorporated in admixture with the first and/or second lipid component.

To further enhance the beneficial effects of the particle, it is preferred that the weight ratio of the first lipid component to the water-swellable or water-soluble polymeric component is in the range from about 0.1 to about 10. In some embodiments, the weight ratio is from about 0.1 to about 5, from about 0.1 to about 3, from about 0.1 to about 2, or from about 0.1 to about 1. In further embodiments, this weight ratio is from about 0.2 to about 1.5, from about 0.25 to about 1.2, from about 0.25 to about 1.0, such as about 0.3, about 0.5., about 0.75, or about 1, respectively. Particularly preferred is a weight ratio from about 0.5 to about 5, or from about 0.75 to about 4, or from about 1 to about 3, respectively.

The inventors have found that the satiety-inducing effect of a free or esterified fatty acid is enhanced if delivered in the form of the particle of the invention, which allows appetite suppression and the prevention and/or treatment of obesity even without pharmacological intervention using a synthetic drug. It is therefore a preferred embodiment that the particle is also free of a synthetic drug substance. In other words, the particle may substantially consist of the water-swellable polymeric or water-soluble component and the first lipid component, and optionally the second lipid component, the amino acid, the vitamin and/or the micro-nutrient and optionally one or more pharmacologically inert excipients such as the hydrophilic component or an inert core material.

The particle according to the invention may be in the form of a granule, a pellet, or a minitablet. More preferably, the particle is a granule and/or a pellet.

As used herein, a granule refers to an agglomerated particle which has been prepared from a plurality of smaller, primary particles. Agglomeration, or granulation, for the purpose of preparing a granule, may involve the use of a dry, wet or melt granulation technique.

A pellet, as used herein, is understood as a particle with a relatively spherical or spheroidal shape. If prepared by an agglomeration process, a pellet is a special type of granule. However, pellets (i.e. spherical or spheroidal particles) may also be prepared by other processes than agglomeration. For the avoidance of doubt, the degree of sphericity of a pellet may differ in various technical fields. In the context of the invention, the sphericity of a pellet is in the typical range of pellets used in pharmaceutical formulations for oral use.

A minitablet, often also referred to as a microtablet, is a unit formed by the compression or compaction of a powder or of granules. Typically, the compression is done on tablet presses using punches.

Minitablets, tablets or capsules comprising the particles of the invention are preferably formulated and processed in such a way that they rapidly disintegrate after oral administration. As used herein, disintegration is understood as a substantial physical change to the minitablet, tablet or capsule morphology, such as the rupture or detachment of the tablet's coating, the dissolution of a capsule or the disintegration of a tablet or minitablet to release particles or pellets or granules of the invention. For the detection of such tablet, minitablet or capsule disintegration behaviour, a microscope may be used. With respect to the apparatus, the hydrodynamic conditions, and the temperature, the method <701> of the United States Pharmacopeia 29 (USP29) may be used, except that water may be used as test medium and that the wire mesh may be adapted with respect to the mesh size or aperture to take the sieve diameter of the tablet, minitablet or capsule into account. When tested according to this method, the minitablets or tablets or capsules comprising particles according to the invention preferably disintegrate within not more than about 15 minutes. More preferably, they disintegrate within about 10 minutes or less. According to another embodiment, they disintegrate within about 8 minutes or less, or within about 5 minutes or less, respectively.

Particles according to the invention may be prepared by a method comprising a step of processing a mixture comprising the first lipid component, the water-swellable or water-soluble polymeric component and optionally the amino acid, the vitamin and/or the micro-nutrient by (a) extruding the mixture using a screw extruder; (b) spray congealing the mixture, optionally using a jet-break-up technique; (c) melt granulating the mixture; (d) compressing the mixture into minitablets; (e) melt injection of the mixture into a liquid medium; or (f) spray coating of the mixture onto inert cores.

The preparation of the mixture comprising the first lipid component, the water-swellable or water-soluble polymeric component and optionally the amino acid, the vitamin and/or the micro-nutrient may be accomplished by conventional means such as blending or high-shear mixing. Optionally, the mixture is prepared using the same equipment which is also utilised for the subsequent step in which the particles are formed. For example, for preparing a melt to be used for melt congealing, melt granulation or melt injection, it may not be required to prepare a dry premix prior to melting the constituents of the melt, but the mixing and melting can be performed simultaneously in one step. Therefore, the mixture to be processed according to steps (a) to (f) above should be broadly interpreted to cover any form of combining the materials required for preparing the particles.

In one embodiment, the mixture is extruded using a screw extruder. Optionally, a twin-screw extruder is used for carrying out the extrusion step. The extruder should have a screen with an aperture that is useful for producing an extrudate with appropriate diameter, such as 0.5 mm or 1.0 mm. The screw speed may be selected in consideration of the capability of the extruder and on the processability of the mixture. For example, it may be useful to select a screw speed in the range from about 20 to about 100 rpm.

Preferably, the extrusion step is carried out without the use of a solvent and at a relatively low temperature, such as below about 35° C., or below about 30° C., e.g. at room temperature. It is also preferred that the extrusion step is carried out at a temperature which is lower than the lower limit of the melting range of the lowest-melting constituent of the mixture.

It is also preferred that the ingredients used for preparing the particles by extrusion are mixed or blended before they are fed to the extruder.

As mentioned above, the ingredients may also be mixed using the same equipment which is utilised for the extrusion step. Thus, it is also preferred that the ingredients used for preparing extruded particles are provided to the extruder by co-feeding, using appropriate feeding equipment, and optionally recycled within the extruder (e.g. via internal bypass-loops) until a uniform mixture is obtained which is ready for subsequent extrusion.

Subsequent to the extrusion step, the extrudate may be spheronised in order to obtain approximately spherical particles. For this purpose, any conventional spheroniser may be used. The temperature of the spheroniser jacket should preferably be set to be lower than the lower limit of the melting range of the lowest-melting constituent of the mixture. The speed of the spheronisation plates may be set between about 200 and about 2,000 rpm, such as about 500 to about 1,500 rpm. Subsequent sieving may be performed in order to select an optimal particle size of the product.

In a particular embodiment, the particles are prepared from the mixture by spray congealing. This process may also be referred to as spray chilling or spray cooling. In this process, a liquid melt is atomised into a spray of fine droplets of approximately spherical shape inside a spray cooling chamber. Here, the droplets meet a stream of air or gas which is sufficiently cold to solidify the droplets. The air or gas stream may have a co-current, mix-current or counter-current direction of flow.

To improve the formation of droplets of appropriate size and shape, a heatable rotary spray nozzle or a fountain nozzle may be used. In the context of the invention, a high speed rotary nozzle is one of the preferred nozzle types for preparing the particles.

Optionally, the uniformity of the atomised droplets may be further enhanced by using a jet break-up technique, such as electrostatic droplet generation, jet-cutting, jet excitation or flow focusing. In general, jet break-up refers to the disintegration of a liquid/gas jet due to forces acting on the jet.

In electrostatic droplet formation processes, a nozzle equipped with an electrode is used which applies an electrical charge to the melt spray. In jet cutting, the spray is directed through a cutter similar to e.g. a rotary disc with apertures of defined size. Jet excitation means the excitation of the melt spray by ultrasonic waves, causing vibration and facilitating the separation of droplets.

Flow focusing results from combining hydrodynamic forces with a specific geometry, which may be achieved by using a pressure chamber pressurised with a continuous focusing fluid supply. Inside, a focused fluid is injected through a capillary feed tube whose extremity opens up in front of a small orifice linking the chamber with the exterior ambient. The focusing fluid stream moulds the fluid meniscus into a cusp giving rise to a microjet exiting the chamber through the orifice. Capillary instability breaks up the stationary jet into homogeneous droplets.

In another specific embodiment, the particles are prepared by injecting the melted mixture into a liquid. The liquid may be cooled to a temperature below room temperature, or preferably to substantially below the lower limit of the melting range of the lowest-melting constituent of the lipid component. The liquid should be selected taking the composition of the mixture into consideration, but also with an eye on safety and physiological tolerability. In many cases, ethanol is a suitable liquid.

In another embodiment, the particles may be formed by melt agglomeration, or melt granulation. In the context of the invention, agglomeration and granulation may be used interchangeably. For this purpose, the constituents of the mixture are mixed or blended and agglomerated, or granulated, in a suitable type of equipment, such as a heatable granulator, a high-shear mixer/granulator or a fluid bed granulator. Depending on the type of equipment, the granulation may be carried out by heating the mixture to a temperature at which at least one of its constituents softens or melts, under continuous stirring or mixing. In a conventional granulator, this may lead to larger agglomerates which are then passed through a sieve to obtain the desired particle size. If fluid bed equipment is used, the complete mixture may be fluidised and heated carefully up to the melting temperature of the lowest-melting constituent. Alternatively, the lowest-melting constituent may be melted and sprayed onto the fluidised powder mixture comprising the remaining constituents.

Optionally, the melt granules may be further processed and compressed into minitablets. For this purpose, it is preferred that the granules are first blended with one or more tablet fillers/binders to enhance the plasticity of the mixture. Moreover, conventional excipients to improve the flow of the granules and reduce their tackiness may also be added before compression. Tableting may be carried out using any conventional pharmaceutical tablet press, such as an eccentric press or a rotary press. Optionally, the press may be equipped with multi-punch tooling so that each compression yields a plurality of minitablets. Punches for very small tablet diameters are preferred, such as between about 1 mm and about 3 mm, such as about 1.5 mm.

In a further embodiment, the particles are prepared by spray coating the mixture comprising the first lipid component and the water-swellable or water-soluble polymeric component onto inert cores. As used herein, an inert core is a particle from a physiologically acceptable material which is suitable for being coated, and which itself does not substantially contribute to the physiological effect of the particles of the invention, i.e. the induction of satiety. Examples of suitable cores include crystals of appropriate size and shape, such as sugar (sucrose) crystals. In one of the preferred embodiments, spherical beads or non-pareils made from sugar, starch, cellulose, in particular microcrystalline cellulose (e.g. Cellets®) are spray coated with the mixture.

The spray coating of the inert cores may, for example, be performed in a fluid bed apparatus. The mixture of the first lipid component and the water-swellable or water-soluble polymeric component may be melted and sprayed onto the fluidised core particles. Optionally, the amino acid, the vitamin and/or the micro-nutrient if present may also be added to this mixture. Alternatively, an aqueous or organic dispersion (or suspension, which is understood as a sub-type of a dispersion) of the mixture is sprayed onto the fluidised cores in such a way that the water or solvent evaporates and the mixture of the first lipid component and the water-swellable or water-soluble polymeric component—and optionally the amino acid, the vitamin and/or the micro-nutrient if present—forms a coating on the inert core particles.

As in all other processes mentioned above, a subsequent step of classifying the resulting particles using a sieve in order to obtain a more uniform particle size distribution may be useful.

For the preparation of particles according to the invention which further exhibit a coating (or second coating covering the first coating) comprising a second lipid component and/or a hydrophilic component but not the water-swellable or water-soluble polymeric component, such second coating may also be applied using conventional pharmaceutical spray coating techniques. In one of the preferred embodiments, fluid bed coating is used for this purpose, using particles according to the invention prepared as described above as active cores which are fluidised, and onto which either a melt or a dispersion/suspension of the second lipid component, or a solution or dispersion/suspension of the hydrophilic component is sprayed. If both the second lipid component and the hydrophilic component are present, they may be applied together in the form of a dispersion/suspension in water or solvent, or as a melt of the lipid in which the hydrophilic component is dispersed.

According to a further aspect of the invention, an ingestible particle is provided which is obtainable by the method as described above.

In a further aspect, the invention provides a solid composition for oral administration comprising a plurality of the particles as described above, or which has been prepared from a plurality of the particles, such as by compressing the particles into tablets. If not compressed into tablets, the particles may in principle be filled into capsules, sachets, stick packs, or containers (e.g. bottles of glass or other materials). In one of the preferred embodiments, the granules are filled into sachets, stick packs, or containers in such a way that a single dose is accommodated in one primary package. Optionally, the composition may comprise the particles along with one or more further inactive ingredients.

If the particles are to be swallowed as such, it is also preferred that they have a mass median sieve diameter in the range from about 0.1 mm to about 3 mm. Also preferred are mass median sieve diameters in the range from about 0.5 mm to about 3 mm, or from about 0.75 mm to about 2.5 mm, or from about 1 mm to about 2 mm. In other preferred embodiments, the mass median sieve diameter may be in the range from about 0.1 mm to about 0.4 mm, from about 0.2 mm to about 0.5 mm, or from about 0.2 mm to about 0.4 mm, respectively.

The presentation and oral administration in the form of particles in sachets, stick packs or containers is also useful as it is preferred that a relatively large amount of the composition is administered as a single dose. In one of the preferred embodiments, a single dose comprises at least about 2 g of the composition, and more preferably at least about 3 g thereof. In another embodiment, a single dose comprises from about 3 g to about 20 g of the composition. In further embodiments, the amount comprised in a single dose is from about 4 g to about 15 g of the composition, or from about 5 g to about 12 g, or from about 5 g to about 10 g, respectively. It is also preferred that the composition exhibits a high contents of the particles of the invention, such as at least about 50%, or at least about 60%, or at least about 70%, or at least about 80% by weight. Particularly preferred is a particle content in the composition of at least about 90%, or at least about 95%, or at least about 98%, such as about 100% by weight.

For the purpose of administration, the composition may be suspended in a liquid or semisolid vehicle. The liquid may simply be water or fruit juice or a dairy beverage or any other, preferably non-carbonated, ingestible liquid. It may optionally be provided together with the composition within a kit. This has the advantage that the nature and amount of liquid are controlled and the administration is more reproducible. The ready-to-use drink suspension may have, for example, a volume in the range from about 30 mL to about 300 mL, or from about 50 mL to about 200 mL.

In a preferred embodiment, the composition of the invention is administered as suspension drink. It was found that the suspension drink of the invention is useful for administering large amounts, such as 1 g or more, of the composition while exhibiting good drinkability and mouth feel. Drinkability of such a suspension drink according to the invention may be assessed by methods used to determine the flowability of wet granular materials. In particular, dynamic measurements of the angle of repose may be taken using a rotating drum apparatus where the whole drum or its bottom and top are transparent or semi-transparent. Such apparatus are commercially available for instance from Mercury Scientific, USA (Revolution Powder Analyzer) and APTIS, Belgium (GranuDruM powder rheometer). In a suitable experimental set up for dynamic measurements of angle of repose of wet granular material comprising aqueous liquid, the drum is preferably made of PTFE (Teflon®) or coated with PTFE or similar anti-adhesive material, and is filled to half of its volume with a suspension of powder or particles. After placing the drum's top and bottom along a horizontal axis, and repeated tapping for even distribution of the drum's contents, the suspension forms a horizontal meniscus of an angle of zero. This may be visually observed and measured by standard methods of angle measurements. Rotating the drum along this horizontal axis may displace the meniscus of the powder suspension to a certain angle before the meniscus of the suspension repositions itself to an angle of almost zero. The displacement of the meniscus from the horizontal may be repeated several times, and a mean value of the dynamic angle of repose may be calculated.

Preferably the suspension drink comprises a plurality of the particles of the invention and at least one aqueous liquid, and the sum of the volume fractions of the particles and the at least one aqueous liquid makes 100 vol-%. Accordingly, the present invention provides a suspension drink, comprising 50 to 75 vol-% of particles according to the invention;

and 25 to 50 vol-% of at least one aqueous liquid; wherein the volume fractions are based on the total volume of the suspension drink. Preferably, the dynamic angle of repose of the suspension drink is less than about 30°.

In a further preferred embodiment, the amounts of particles and liquid are selected such that a densely packed suspension drink is obtained by matching the filling height of the particles settled in a suitably sized container with the filling height of the aqueous liquid in the same container comprising the settled particles. In other words, the amount of the liquid is chosen in such manner that the meniscus of the liquid is roughly at the position of the upper limit of the settled particles.

The at least one aqueous liquid further may comprise alcohol, flavouring compounds, colouring compounds, preservatives, viscosity enhancers, health ingredients or mixtures of two or more thereof. Suitable flavouring compounds are citric acid, malic acid, phosphoric acid, tartaric acid, natural and synthetic aroma, sweeteners, for example monosaccharides, disaccharides, polyhydric alcohols; including arabitol, erythritol, glycerol, isomalt, lactitol, maltitol, mannitol, sorbitol or xylitol; or sugar substitutes, including cyclamate, saccharine, stevia, sucralose and/or aspartame. Further suitable flavouring compounds are juices of fruits and/or vegetables. Colouring compounds suitable for the aqueous liquid are for example Allura Red AC, Anthocyanine, azorubine, betanin, Brilliant Blue FCF, carotene, Quinoline Yellow WS, Ponceau 4R, Green S, Patent Blue V and tartrazine, either as such or in the form of the corresponding aluminium lakes. Suitable preservatives are vitamins A, E or C, retinyl palmitate, cysteine, methionine, citric acid, sodium citrate, used in amounts of 0.001 to 0.1% by weight based on the liquid.

The amount of the first lipid component, which is a key ingredient of the composition, should preferably be at least about 1 g per single dose or per package. In another embodiment, a single dose comprises at least about 2 g of the first lipid component, such as about 3 g or about 4 g. In a further preferred embodiment, the content of the first lipid component per single dose is at least about 5 g.

The amount of the amino acid (or of the total amino acids, if a mixture or combination of amino acids is used) may be about 0.05 g or more per single dose or per package. In another embodiment, a single dose comprises at least about 0.1 g, or at least about 0.2 g, or at least about 0.5 g of amino acid(s), respectively. In further embodiments, the content of the amino acid(s) per single dose is from 0.5 g to about 5 g, or from 0.5 g to about 3 g.

In one of the embodiments, the components of the particles are selected such that the dynamic angle of repose of a suspension prepared from suspending the composition in water at a weight ratio of 1 is less than 30°.

As mentioned, the particles and the compositions of the invention may be used for the suppression of appetite, in particular in human subjects, and for the induction of satiety. Thus, the invention provides a method of inducing satiety in a subject, wherein the method comprises a step of orally administering a composition comprising an effective amount of a first agent capable of inducing satiety, and a second agent capable of augmenting the satiety-inducing effect of the first agent, and wherein the first and the second agent are optionally selected as described above.

Without wishing to be bound by theory, it is currently believed by the inventors that the appetite suppressing effect is at least in part based on the fatty acid compound comprised in the first lipid component, which upon ingestions interacts with physiological targets located in the mucosa of the gastrointestinal tract, such as in the stomach and/or duodenum, thereby activating one or more signalling cascades which eventually produce a perception of satiety or a reduction of appetite or hunger. Possibly, one of the targets at which the fatty acid acts are the ghrelin cells (or ghrelin receptors), large numbers of which are located in the stomach and the duodenum.

If present, the amino acid may further contribute to the appetite suppressing effect, which may be due to a stimulation of chemosensors in the proximal gastrointestinal tract by which in turn the CCK and glucagon secretion is triggered.

The water-swellable or water soluble polymeric component was found by the inventors to enhance the effect of the fatty acid, which is possibly due to the swelling and/or mucoadhesive properties effecting a prolonged attachment of the particles (or components thereof) to the gastric or duodenal mucosa, allowing for an increased interaction of the fatty acid with the target structure. Of course, other properties of the particles may also effect or contribute to a prolonged gastric residence time, such as the selected particle size or the low density resulting from the high lipid content. In any case, the inventors found that the oral administration of the particles to volunteers induced satiety with the consequence that the subjects experienced suppressed appetite and showed a reduced food intake during the meal following the administration of a composition comprising the particles as described herein. This effect was consistent with animal data showing the composition leads to a weight loss, or weight reduction, of the test animals.

According to a related aspect, the invention provides a method of treating or preventing overweight, obesity, or a disease or condition associated with overweight or obesity in a subject, wherein the method comprises a step of orally administering a composition comprising an effective amount of a first agent capable of inducing satiety, and a second agent capable of augmenting the satiety-inducing effect of the first agent, and wherein the first and the second agent are optionally selected as described above. Moreover, the invention provides a method of treating or preventing overweight, obesity, or a disease or condition associated with overweight or obesity in a subject, which method is also characterised by a step of orally administering a composition comprising an effective amount of the first agent and of the second agent.

Of course, also the preferred particles and/or compositions as described above may therefore be used clinically, or as dietary supplements, for the prevention and/or treatment of obesity and overweight, as well as the prevention and/or treatment of diseases or conditions associated with obesity; e.g. by using the ingestible particles as defined herein and/or compositions comprising or prepared from a plurality of these particles for body weight reduction.

In other words, one aspect of the invention provides a method for the prevention and/or treatment of obesity and overweight, as well as the prevention and/or treatment of diseases or conditions associated with obesity, for appetite suppression, body weight reduction and/or for the induction of satiety, said method comprising a step of orally administering the particles of the invention and/or compositions comprising or prepared from a plurality of these particles. Optionally said method comprises the oral administration of the particles and/or compositions at least once a day over a period of at least one week.

In yet other words, one aspect of the invention provides the use of the particles of the invention and/or compositions comprising or prepared from a plurality of these particles in the manufacture of medicaments for the prevention and/or treatment of obesity and overweight, as well as the prevention and/or treatment of diseases or conditions associated with obesity, for appetite suppression, body weight reduction and/or for the induction of satiety. Optionally, this comprises the oral administration of the particles and/or compositions at least once a day over a period of at least one week.

As used herein, obesity is a medical condition in which excess body fat has accumulated to the extent that it may have an adverse effect on health. Overweight is understood as a borderline condition characterised by a body mass index (BMI) between 25 and below 30. Starting from a BMI of 30, the condition is classified as obesity.

In one embodiment, the particles and/or compositions are administered to normal weight or overweight subjects gaining weight over time or otherwise being at risk of developing obesity. In this case, the therapeutical objective is to stop or limit the weight gain and prevent the development of obesity. Another purpose may be to reduce the risk that the subject develops a disease or condition associated with or caused by obesity.

In a further embodiment, the particles and/or compositions are administered to obese patients in order to treat or reduce the severity of obesity. Again, the therapeutic use may also be directed to the reduction of the risk of developing a disease or condition associated with or caused by obesity.

A large number of diseases and conditions are nowadays considered to be associated with or caused by obesity, even though the mechanism by which they are linked to obesity may not always be fully understood. In particular, these diseases and conditions include—without limitation—diabetes mellitus type 2, arterial hypertension, metabolic syndrome, insulin resistance, hypercholesterolaemia, hypertriglyceridaemia, osteoarthritis, obstructive sleep apnoea, ischaemic heart disease, myocardial infarction, congestive heart failure, stroke, gout, and low back pain. The prevention and/or reduction of risk for developing any of these conditions is within the scope of the therapeutic use according to the invention.

Moreover, the therapeutic use preferably involves the at least once daily oral administration of the particles and/or compositions of the invention over a period of at least one week. In this context, the expression "therapeutic use" is understood to also cover the preventive or prophylactic use. In a further preferred embodiment, the particles and/or compositions are administered to a human subject over a period of at least about 2 weeks, or at least about 4 weeks, or at least about 6 weeks, or at least about 2 months, respectively. Also preferred is an administration regimen providing for once or twice daily administration.

The time of administration should be selected to maximise the satiety-inducing effect on the amount of food which is subsequently taken up by the subject that is treated. For example, it is useful to administer a dose of the composition before a major meal, such as before a lunchtime meal and/or before the evening dinner such as to reduce the amount of food eaten during either of these meals. With respect to the precise timing, it is preferred that the dose is administered within about 5 to 120 minutes prior to the respective meal, in particular about 10 to about 120 minutes prior to the meal, or about 15 to about 90 minutes prior to the meal, such as about 30 or about 60 minutes prior to the meal.

In one of the particularly preferred embodiments, a dose comprising at least about 5 g of the first lipid component is administered to a human subject at least once daily between about 15 and about 90 minutes prior to a meal over a period of at least 4 weeks for the prevention or treatment of obesity or an associated disease.

The invention further provides a method of inducing satiety in a subject, or method of treating or preventing overweight, obesity, or a disease or condition associated with overweight or obesity in a subject, or method of controlling or reducing the body weight of a subject, each method comprising a step of orally administering a composition comprising an effective amount of a first agent capable of inducing satiety and a second agent capable of augmenting the satiety-inducing effect of the first agent, wherein the methods further comprise the use of a device for the collection, storage and/or display of information relating to a subject's adherence to, or the effectiveness of, a predefined therapeutic regimen of orally administering the composition.

According to a related aspect, the invention provides a body weight management system comprising the composition comprising effective amounts of the first agent and the second agent, and a device configured for the collection, storage and/or display of information relating to a subject's adherence, or the effectiveness of, a predefined therapeutic regimen of orally administering the composition.

In more detail, it is contemplated that the particles and/or compositions of the invention are used in combination with the use of a device for the collection, storage and/or display of information relating to a subject's adherence to the therapy and/or the effectiveness of the therapy. As used herein, information relating to a subject's adherence to the therapy may include, for example, information on whether a dose was administered within a certain period of time (e.g. during a calendar day), or the time at which each dose was administered. The device is preferably a programmed electronic device, such as a computer, in particular a microcomputer, and most preferably a portable microcomputer such as a mobile phone ("smartphone"), or a wearable device such as a smart watch, an electronic wristband, or the like. The information may be received by the device automatically from a sensor, or it may be entered manually by a user, such as the subject or patient, the physician, nurse, or by a caregiver, and stored for subsequent analysis or display. For example, the patient may periodically monitor his or her actual compliance or adherence to the therapy.

The device may be programmed to provide the user with a feedback signal or reminder in case of non-compliance or lack of adequate adherence to the therapy. The feedback signal may be optical, haptic (e.g. vibration), or acoustic.

Information relating to the effectiveness of the therapy may include, for example, the weight of the subject, the degree of hunger or appetite, the number of meals and snacks, or the type or amount of food eaten during any particular period of time (e.g. a calendar day), or even physiological data such as the blood glucose concentration or blood pressure. Depending on its type, the information relating to the effectiveness of the therapy may be automatically received by the device or entered manually by the user. Information with respect to the feeling of satiety or hunger may be usefully entered by the user or patient in a manual mode, whereas physiological parameters such as blood glucose or blood pressure may be received from the respective measuring devices used for their determination. In the latter case, the transfer of the data encoding the information generated by the measuring device to the device for the storage and/or display of the information is preferably wireless.

In more detail, information collection may be user-initiated or the device may be programmed with an application (i.e. software) which creates an alert calling for the user to input her or his satiety-state information. Preferably, information collection proceeds in regular time intervals such as 15 or 30 min intervals. In one embodiment, information collection is performed throughout a period of 12, 16 or 18 hours per day. In another embodiment, information collection is performed in multiple periods of for instance 1 to 3 hours over the day, for instance three times for 3 hours each. Preferably such time periods cover meal times such as breakfast, lunch and dinner. Preferably, users—for a given period of information collection—may not refer to previous satiety ratings when providing the real-time information.

Information collection may proceed in the following fashion. After the user has opened the software application, a satiety state screen is displayed on the colour touch screen using visual analogue scales for the assessment of satiety. Such scales and scores have previously been described in detail [Flint A, Raben A, Blundell J E, Astrup A. Reproducibility, power and validity of visual analogue scales in assessment of appetite sensations in single test meal studies. Int J Obes Relat Metab Disord 2000; 24:38-48). In brief, the visual analogue scale (VAS) consists of a horizontal, unstructured, 10 cm line with words anchored at each end, describing the extremes ('not at all' or 'extremely') of the unipolar question, 'How satiated are you right now?' To ensure reliable and valid results, participants rate their feeling of satiation as precisely as possible, and they cannot refer to their previous ratings when marking the VAS.

The satiety state screen may display a query 1 "how hungry do you feel?" combined with an unstructured sliding scale labelled "I am not hungry at all" on one end to "very hungry" on the other hand. The application will wait for the user to touch the sliding scale at one position. Upon touching the scale, a slider may appear, and the user may adjust its position. The application will determine the position of the slider after the user removed its touching finger from the slider symbol, retrieve the positional value and use it for further processing.

Further potentially useful embodiments are easily derivable on the basis of the guidance provided herein-above and the following examples.

EXAMPLES

Example 1: Preparation of Particles by Spray Congealing

Particles with a water-swellable or water-soluble polymeric component embedded within a lipid component may be prepared by spray congealing as follows. 250 g of capric acid are melted. 100.0 g of carbomer homopolymer type A NF and 50.0 g of sodium caprate are added to the melt and mixed such as to form a viscous suspension. Under continuous heating, the suspension is fed to the heated rotary nozzle of a spray congealing tower. Cold air is continuously introduced into the tower to allow solidification of the resulting droplets. The solid particles are then passed through appropriate sieves to allow removal of oversize and undersize particles, and to obtain particles according to the invention. Optionally, the product may be further processed, e.g. by coating the particles.

Example 2: Preparation of Particles by Spray Congealing

Similarly, particles may be prepared from polycarbophil and a mixture of fatty acids. For example, 240.0 g of lauric acid and 60.0 g of capric acid are melted, and 100.0 g of polycarbophil (USP) are incorporated into the melt such as to obtain a viscous lipid suspension. Under continuous heating, the suspension is fed to the heated rotary nozzle of a spray congealing tower. Again, cold air is continuously introduced into the tower to allow solidification of the resulting droplets. Subsequently, the solidified particles are passed through appropriate sieves to allow removal of oversize and undersize particles, and to obtain particles according to the invention.

Example 3: Preparation of Particles by Spray Congealing Using Jet Break-Up Techniques As a variation of Example 1, a spray congealing tower may be used which is equipped for a jet break-up spray process to generate monodisperse particles of appropriate size, e.g. electrostatic droplet generation, jet-cutter technology, jet excitation, or flow focusing.

200.0 g of hard fat EP/NF (e.g. Suppocire® A) and 400.0 g of sodium myristate are mixed and melted. 100.0 g of carbomer homopolymer type B NF added to the melt and mixed such as to form a viscous suspension. Under continuous heating, the suspension is fed to a nozzle of a spray congealing tower with jet excitation equipment. The vibration excitation is set to provide particles in the range of 200 µm. Cold air is continuously introduced into the tower to allow solidification of the resulting droplets. The uniform, solidified particles are collected as final product.

Example 4: Preparation of Particles by Melt Injection 150.0 g of a mixture of hard fat EP/NF and glyceryl monooleate (type 40) EP/NF (e.g. Ovucire® WL 2944) and 200.0 g of sodium laurate are mixed and melted. 90.0 g of carbomer interpolymer type A NF added to the melt and mixed such as to form a viscous suspension. Under continuous heating, the suspension is fed to the needle of an elementary microfluidics device, through which droplets are formed and injected into cooled absolute ethanol to provide particles in the 250 µm range. The solidified particles are collected and thoroughly dried to result in the final product.

Example 5: Preparation of Particles by Solvent-Free Cold Extrusion

An intimate mixture of 250.0 g of hardened palm oil, 50.0 g of sodium oleate and 110.0 g of carbomer 941 NF is prepared using a V-blender. The blend is fed by a gravimetric powder feeder type KT20 (K-Tron) to the powder inlet opening of a Leistritz NANO 16® twin screw extruder and extruded in the first segments at a temperature range between 25° C. and 30° C. The final segment is cooled to 20° C. Short rods of approx. 0.8-1.5 mm length are obtained by this process. The rods are subsequently spheronised in a Caleva® MBS 120 equipment, with water jacket temperature set to 30-35° C., until the final product is obtained in the form of essentially spherical particles.

Example 6: Coating of Sugar Crystals by Melt Granulation

A premix of 200.0 g of myristic acid, 75.0 g of sodium oleate, 100.0 g of carbomer 941 NF and 250.0 g of sucrose crystals (mean particle size 200-250 µm) is prepared. The premix is introduced into a planetary mixer equipped with a heatable jacket. Under continuous operation of the mixer, the temperature is slowly raised until the lipid phase is thoroughly molten. Again under continuous operation of the mixer, the temperature is cooled to room temperature. The resulting solidified mass is passed through a sieve to break or remove oversized particles, giving the final product.

Example 7: Coating of Non-Pareil Seeds by Organic Lipid Solution

A premix of 200.0 g of myristic acid, 75.0 g of sodium oleate, and 100.0 g of carbomer 941 NF is prepared and dispersed in absolute ethanol. 275.0 g of sugar spheres EP/NF (non-pareils) are introduced into an explosion-proof fluid bed equipment with Wurster column and pre-heated to 50-55° C. Subsequently, the dispersion is slowly sprayed on pre-heated sugar spheres, allowing for evaporation of the ethanol, and taking into account the critical explosion limit of air-ethanol mixtures. At the end, the coated sugar spheres are cooled to room temperature and flushed with cold air until the limit of residual solvents is within acceptable limits, to provide the final product.

Example 8: Coating of Non-Pareil Seeds by Aqueous Suspension

A premix of 300.0 g of myristic acid and 100.0 g of carbomer 941 NF is prepared and dispersed in demineralised water (q.s.). In analogy to the previous example, 275.0 g of sugar spheres EP/NF (non-pareils) are introduced into a fluid bed equipment with Wurster column and pre-heated to approx. 50-55° C. Subsequently, the suspension is slowly sprayed on the pre-heated sugar spheres to allow the water to evaporate. At the end, the coated sugar spheres are cooled to room temperature and flushed with cold air until the limit of residual water is within acceptable limits, to provide the final product.

Example 9: Compression of Minitablets from Melt Granulate

Particles according to the invention may also be prepared in the form of minitablets, preferably with a small diameter, such as 1.5 mm. For example, 300.0 g of lauric acid, 50.0 g of sodium laurate, 100.0 g of microcrystalline cellulose (e.g. Avicel® PH101), and 100.0 g of carbomer 941 NF are mixed to obtain a premix which is then introduced into a jacketed, heated planetary mixer, and agglomerated to result in a granular material. The melt granulate is then sieved through an appropriate sieve equipped with knives to result in a fine, granular material. This granular material is subsequently blended with 75.0 g of microcrystalline cellulose (e.g. Avicel® PH101). The resulting blend is compressed on a multi-punch eccentric tablet press into biconvex tablets with a diameter of 1.5 mm and thickness of approx. 2 mm, to provide the final product. In this example, the microcrystalline cellulose may also be replaced by lactose (e.g. lactose monohydrate NF) or calcium hydrogen phosphate dihydrate (Ph.Eur.).

Example 10: Coating of Active Cores with a Film Coating Based on Hypromellose Active cores prepared according to Examples 1 to 9 may be coated as follows. An aqueous polymer solution (A) is prepared by dissolving 5.0 g of hypromellose type 2910 (e.g. Pharmacoat® 603) in 90.0 mL of demineralised water.

Separately, a pigment dispersion (B) is prepared by dispersing 2.0 g of titanium dioxide (e.g. Titanium Dioxide "Anatas") and 1.0 g of a pigment in 15.0 mL of demineralised water, followed by homogenisation using a high-shear homogeniser. Subsequently, a coating dispersion (C) is prepared by mixing the polymer solution (A) and the pigment dispersion (B) under continuous stirring.

In the next step, 1,000 g of the active cores prepared according to any one of Examples 1 to 9 are fluidised in a fluidised bed granulation apparatus equipped with a Wurster column at a temperature of 25-30° C. 100 mL of the coating dispersion (C) are slowly sprayed on the active cores, keeping the bed temperature at 25-30° C. by adjusting inlet air temperature and spray rate. The coated active cores are fully dried at the same temperature within the fluidised bed, and thereafter cooled to room temperature within the fluidised bed.

In result, coated particles will be obtained whose coating rapidly disintegrates after oral ingestion.

It is noted that the polymer solution (A) may also be prepared by dissolving 5.0 g of hypromellose type 2910 (e.g. Pharmacoat® 603) in a mixture of 45.0 mL of ethanol and 55.0 mL of demineralised water. This variation would lead to a more rapid evaporation of the solvent during the spray coating process.

Alternatively, a coating dispersion may also be prepared by further incorporating a plasticiser, a surfactant, and a small amount of ethylcellulose. In this case, a polymer solution (A) may be prepared by dissolving 5.0 g of hypromellose type 2910 (e.g. Pharmacoat® 603) and 0.5 g of triacetin (glycerol triacetate) in 50.0 mL of demineralised water. In addition, 0.25 g of sodium lauryl sulphate are dissolved in 2.5 mL of demineralised water to form a surfactant solution (A'). A pigment dispersion (B) is prepared by dispersing and homogenising 2.5 g of talc, 3.0 g of titanium dioxide and 0.2 g of colorant pigment in 20.0 mL of demineralised water. Subsequently, the coating dispersion (C) is prepared by mixing the polymer solution (A), the surfactant solution (A'), the pigment dispersion (B), and 5.0 g of an ethylcellulose dispersion (corresponding to 1.5 g dry matter). The coating procedure itself is conducted as described above.

Example 11: Preparation of a Composition Comprising Coated Particles

A composition comprising the particles of the invention which may easily be filled into stick packs or sachets may be obtained from gently mixing 1,005 g of the coated active cores prepared according to Example 10 with 0.5 g of hydrophobic colloidal silica (NF) (e.g. AEROSIL® R 972) in a rotating drum. Instead of hydrophobic colloidal silica, a standard grade of colloidal silicon dioxide (e.g. AEROSIL® 200) may also be used at the same amount. In this composition, the silica acts as anti-tacking agent.

Example 12: Coating of Active Cores with a Mixture of a Lipid Component and a Hydrophilic Component A coating dispersion is prepared by dissolving 5.0 g of hypromellose type 2910 (e.g. Pharmacoat® 603) and dispersing 2.0 g of lauroyl polyoxyl-32 glycerides NF (e.g. Gelucire® 44/14) in a mixture of 45.0 mL of ethanol and 55 mL of demineralised water. Subsequently, 105 mL of the dispersion is coated on 1,000 g of the active cores prepared according to any one of Examples 1 to 9, using the same equipment and procedure as in Example 10. Coated particles according to the invention are provided which exhibit rapid disintegration of the coating after oral administration.

As alternatives to the lauroyl polyoxyl-32 glycerides NF, similar amounts of stearoyl polyoxyl-32 glycerides NF (e.g. Gelucire® 50/13) or caprylocaproyl polyoxyl-8 glycerides NF (e.g. Labrasol®) may be used.

Example 13: Coating of Active Cores with a Film Coating Based on Povidone

A coating solution may be prepared by dissolving 5.0 g of povidone K30 and 1.0 g of polyethylene glycol 4000 (alternatively polyethylene glycol 1000) in a mixture of 60 mL of ethanol and 40 mL of demineralised water. 100.0 mL of the solution are then sprayed onto 1,000 g of the active cores prepared according to any one of Examples 1 to 9, using the same equipment and procedure as in Example 10. The procedure leads to particles whose coating rapidly releases the active core after oral administration.

Example 14: Coating of Active Cores with a Film Coating Based on Ethyl Cellulose A coating solution may be prepared by dissolving 4.0 g of ethylcellulose NF (e.g. ETHOCEL® 10 FP) and 1.0 g of polyethylene glycol 4000 in a mixture of 25 mL of acetone, 35 mL of ethanol and 40 mL of demineralised water. 100.0 mL of the solution are then sprayed onto 1,000 g of the active cores prepared according to any one of Examples 1 to 9, using the same equipment and procedure as in Example 10, and taking into account the critical explosion limit of air-acetone-ethanol mixtures. The procedure leads to particles whose coating rapidly releases the active core after oral administration.

Example 15: Coating of Active Cores with a Coating Based on Phospholipids

In this Example, the coating comprises a lipid component in combination with a hydrophilic component. A coating suspension is prepared by dispersing 10.0 g of partially hydrogenated soybean lecithin (e.g. Lipoid S75-35 or Lipoid S-PC-35) in demineralised water (q.s.), using high shear homogenisation, followed by the addition of a small amount (q.s.) of an immediate release coating system (e.g. Opadry®) containing a water-soluble coating polymer, a plasticiser and pigment. 100.0 mL of the dispersion are then sprayed onto 1,000 g of the active cores prepared according to any one of Examples 1 to 9, using the same equipment and procedure as in Example 10. The procedure leads to particles whose coating rapidly releases the active core after oral administration.

To obtain coated particles with reduced stickiness, a portion of the partially hydrogenated soybean lecithin may be replaced by a fully hydrogenated lecithin (e.g. Lipoid S75-3), or 2.0 g of the fully hydrogenated lecithin may be incorporated in addition to the 10.0 g of partially hydrogenated soybean lecithin.

Example 16: Coating of Active Cores with a Mixture of Lecithin and Maltodextrin 10.0 g of a powder mixture of lecithin and maltodextrin (e.g. Soluthin®) is dispersed in 95 mL of demineralised water at room temperature. 1,000 g of the cores prepared according to any one of Examples 1 to 9 are fluidised bed apparatus at a temperature of 20 to 30° C. Subsequently, 100.0 mL of the dispersion are slowly sprayed on the active cores by the top spraying procedure, keeping the bed temperature at 20-30° C. by adjusting inlet air temperature and spray rate. The coated cores are fully dried at the same temperature within the fluidised bed, and thereafter cooled to room temperature within the fluidised bed. Again, coated particles are obtained which release their active core rapidly after oral administration.

Example 17: Coating of Active Cores with a Sucrose Ester

A clear solution is prepared by dissolving 15.0 g of sucrose laurate L-1695 in 90.0 mL of demineralised water at room temperature. 1,000 g of the active cores prepared according to any one of Examples 1 to 9 are fluidised and coated in a similar manner as described in Example 16 to obtain coated particles with similar properties with respect to their release behaviour.

As an alternative to sucrose laurate L-1695, sucrose laurate L-1570 may be used, optionally in the form of sucrose laurate LWA-1570, a ready-to-use solution of 40% L-1570 in 4% ethanol and 56% water. For example, 30.0 g of sucrose laurate LWA-1570 may be diluted with 110.0 mL of demineralised water and 20 mL of ethanol. 150 mL of this coating solution may be used to coat 1,000 g of the cores.

Example 18: Coating of Active Cores with Ethylene Glycol/Vinyl Alcohol Graft Copolymer Coated particles according to the invention may also be prepared by using ethylene glycol/vinyl alcohol graft copolymer as an immediate release coating agent. For instance, a polymer solution may be prepared from 24.0 g of Kollicoat® which are dispersed 96 mL of demineralised water and dissolved under stirring. Separately, a pigment suspension is prepared by dispersing 4.5 g of talc, 1.5 g of iron oxide red, and 3.9 g of titanium dioxide in 11.0 mL of demineralised water, followed by homogenisation with a high shear homogeniser. The coating dispersion is then obtained by mixing 100.0 mL of the polymer solution with 20.0 g of the pigment suspension. 1,000 g of the active cores prepared according to any one of Examples 1 to 9 are fluidised and coated in a similar manner as described in Example 16 to obtain coated particles with similar properties with respect to their release behaviour. During the whole coating process, the coating suspension is continuously stirred to avoid sedimentation.

Example 19: Preparation of Particles by Cryomilling 300 g hard fat (adeps solidus from Caelo, Germany) were brought to a melt at 50° C. 200 g Carbopol® 971G (Lubrizol) were incorporated into the lipid by means of a spatula. The viscous mass was filled into a plastic bag and cooled to −18° C. in a freezer. The frozen material was crushed with a hammer and shredded to a powder in a kitchen blender (Bosch ProfiMIXX, Germany). After drying under vacuum at 25° C. to remove residual condensed water, the obtained particles were classified through a set of wire mesh sieves (VWR International, Germany) to provide a classified powder having a size of below 0.5 mm.

Example 20: Preparation of Particles by Cryomilling 500 g hard fat (Witepsol® W35 from NRC, Germany) were brought to a melt at 50° C. 250 g Carbopol® 971G (Lubrizol) were incorporated into the lipid by means of a spatula. The viscous mass was filled into a plastic bag and cooled to −18° C. in a freezer.

The frozen material was crushed with a hammer and shredded to a powder using an ultra-centrifugal mill (ZM 200, Retsch, Germany). For milling, the material was pre-cooled using dry ice, and a rotation speed of 18000/min was applied for two minutes. The material was quantitatively converted to particles with a diameter (D90) of 0.2 mm. Prior to classifying the particles, they were dried under vacuum at 25° C. to remove residual condensed water, where this was considered expedient.

Example 21: Preparation of Particles by Fluid-Bed Granulation 400 g of the classified powder from Example 19 were loaded into a fluid bed device (Ventilus V-2.5/1 from Innojet, Germany) equipped with a IPC3 product reservoir. The powder was fluidised at 32° C. using an air flow of 50 m³/h. The material was granulated for 30 min and classified through a set of wire mesh sieves to obtain 240 g of particles of a size between 0.5 and 1.0 mm, and 64 g of particles of a size above 1.0 mm.

Example 22: Animal Studies

A. General Procedures

Animals (rats) were kept in cages on standard animal bedding (two animals per cage or individual housing) and were provided with ad libitum access to food and water. Animal food was provided as pellets in a pellet rack or as a cream or as granulate powder in a container attached to the inside of the cage.

Body weight was recorded at beginning and end of experiments. Food consumption was documented daily except for weekends. Experiments were performed according to German laws of animal protection.

Rodent chow was purchased from Ssniff® Spezialdiaten GmbH, Germany and poly(acrylic acid) (PAA, Carbopol® 971 P NF) was obtained from the Lubrizol Corporation, USA. Cocoa butter chips (Caelo 633B) were from Caesar & Lorentz, Germany. Hard fat (Witepsol®) was from NRC, Germany. All percentages provided are w/w-percentages, unless specifically mentioned otherwise.

B. Standard Pellet Chow with 5% Fat—Reference for Normal Food Uptake and Weight Gain Twelve male wistar rats having a mean body weight of 319±7 g were fed an experimental diet provided as pellets for seven days. The mixture was composed of standard chow diet (Ssniff® EF R/M Control, 5%) having a fat content of 5% in the final mixture.

Water was added to the standard chow to produce a paste which was extruded and cut into pellets (1 cm×3 cm) by means of a food processor (Kitchen Aid Classic, USA). Pellets were dried at 25° C. over night.

At the end of the experiment, food intake, energy intake and body weight change were calculated (±SD). Animals gained 5.0±1.9% body weight, mean daily food intake was 24.3±2.7 g, representing a mean metabolisable energy intake of 374±40.8 kJ per animal per day.

C. Pellet Chow/Cocoa Butter Composition with 11.6% Fat—Reference for Calorie-Adjusted Food Uptake Six male wistar rats having a mean body weight of 324±6 g were fed an experimental diet provided as pellets for six days. The mixture was composed of standard chow diet (Ssniff® EF R/M Control, 5%) and cocoa butter (7.5% relative to the standard chow weight), resulting in approx. 11.6% fat in total (including cocoa butter) and approx. 7.0% cocoa butter relative to the final mixture. Cocoa butter was melted and blended with standard chow. Water was added to produce a paste which was extruded and cut into pellets (1 cm×3 cm) by means of a food processor (Kitchen Aid, USA). Pellets were dried at 25° C. over night.

At the end of the experiment, food intake, energy intake and body weight change were calculated (±SD). Animals gained 3.8±1.3% body weight, mean daily food intake was 22.5±2.0 g, representing a mean metabolisable energy intake of 382.2±33.7 kJ per animal per day.

D. Cream- or Paste Chow Composition with 50% Fat Limited to 10 g/Day Per Animal—Reference for Weight Loss Induced by Restricted Energy Supply Four male wistar rats having a mean body weight of 329±7 g were fed an experimental diet provided as a mix of creamy, paste-like texture for five days. The experimental diet was a high-fat chow composition comprising 50% fat relative to the final mixture, which was prepared by blending three standard chow diets as obtained from Ssniff®, namely 'EF R/M Control, 5%', 'EF R/M with 30% fat' and 'EF R/M with 80% fat', in a weight ratio of 10:45:45, respectively.

Chow supply was limited to 10 g per day representing a mean metabolisable energy intake of 236 KJ per day. At the end of the experiment, body weight change was evaluated (±SD). Animals lost 3.6±0.6% body weight.

E. Pellet Chow Composition with 4.5% Fat and 9.1% Polymers—Example for Polymer—Induced Weight Loss Due to Reduced Uptake Six male wistar rats having a mean body weight of 301.4±9.2 g were fed an experimental diet provided as pellets for seven days. The mixture was composed of standard chow diet (Ssniff® EF R/M Control, 5%) and in total 10% polymers (relative to the standard chow weight; specifically 6.2% Carbopol® 971 NF, 1.5% Kollicoat® MAE 100P from Sigma-Aldrich, USA, and 2.3% chitosan from crab shells, Sigma-Aldrich, USA). This resulted in a pellet chow composition with approx. 4.5% fat and approx. 9.1% total polymers relative to the final mixture (specifically, approx. 5.6% Carbopol®, approx. 1.4% Kollicoat® and approx. 2.1% chitosan).

Standard chow was mixed with polymer powders. Water was added to produce a paste which was extruded and cut into pellets (1 cm×3 cm) by means of a food processor (Kitchen Aid, USA). Pellets were dried at 25° C. over night.

At the end of the experiment, food intake, energy intake and body weight change were evaluated (±SD). Animals lost 3.9±4.6% body weight, mean daily food intake was 18.1±2.1 g, representing a mean metabolisable energy intake of 253±29 kJ per animal per day.

F. Pellet Chow Composition with 4.7% Fat and 5.7% Polymer—Example for Polymer—Induced Weight Loss Due to Reduced Uptake Six male wistar rats having a mean body weight of 317±14.5 g were fed an experimental diet provided as pellets for seven days. The mixture was composed of standard chow diet (Ssniff® EF R/M Control, 5%) and 6% Carbopol® 971 NF (relative to the standard chow weight), resulting in a pellet chow composition with approx. 4.7% fat and approx. 5.7% Carbopol® relative to the final mixture.

Standard chow was mixed with polymer powder, water was added to produce a paste which was extruded and cut into pellets (1 cm×3 cm) by means of a food processor (Kitchen Aid, USA). Pellets were dried at 25° C. over night.

At the end of the experiment, food intake, energy intake and body weight change were calculated (±SD). Animals lost 1.8±2.3% body weight, mean daily food intake was 18.4±5.3 g, representing a mean metabolisable energy intake of 267±77 kJ per animal per day.

G. Powdered Pellet Chow/Witepsol® Composition with 11.0% Fat and 5.3% Polymer—Example for Polymer-Induced Weight Loss Due to Reduced Uptake Six male wistar rats having a mean body weight of 307±8 g were fed an experimental diet provided as powder for five days. The mixture was composed of standard chow diet (Ssniff® EF R/M Control, 5%) and Witepsol® W25 (7.5% relative to standard chow weight) and 6% Carbopol® 971 NF (relative to standard chow weight), resulting in approx. 11.0% fat in total (including Witepsol®), approx. 6.6% Witepsol® and approx. 5.3% Carbopol® relative to the final mixture.

Molten Witepsol® was mixed with polymer powder, transferred into a zip-loc-bag and cooled to −18° C. in a freezer. The material was crushed by means of a hammer and shredded to a granulate in a kitchen blender (ProfiMIXX, Bosch, Germany). Standard chow diet was added and mixed with the granulate to obtain a powder diet.

At the end of the experiment, food intake, energy intake and body weight change were calculated (SD). Animals lost 2.4±1.8% body weight, mean daily food intake was 15.1±0.8 g, representing a mean metabolisable energy intake of 245±13 kJ per animal per day.

Example 23: Breath Tests on Healthy Volunteers

Gastrointestinal half-life and bioavailability of free fatty acids were assessed using the $^{13}$C-octanoic acid breath test. The labelled octanoic acid substrate is rapidly absorbed in the intestine and metabolised in the liver with the production of $^{13}CO_2$, which is exhaled, thus reflecting uptake of octanoic acid from the gastrointestinal tract and after exit from the stomach. At the beginning of the experiment a reference breath sample was taken from the subject. Subsequently, the subject consumed a load of either lipid granulate as reference sample, or lipid granulate containing polymers as test sample.

Granulate was prepared by melting lipid at 50° C. and adding 100 mg of $^{13}$C octanoic acid (Campro Scientific, The Netherlands), and—for test samples—incorporating polymer. The mixture was subsequently transferred into a zip-loc-bag and cooled to −18° C. in a freezer. The material was crushed by means of a hammer, shredded to a granulate in a kitchen blender (Bosch, Germany), dried under vacuum at 25° C. and classified through a set of wire mesh sieves (VWR International, Germany) to a granulate size of below 1.3 mm and above 0.5 mm.

For sample ingestion, frozen granulate was mixed with 100 g cold yogurt (fruit flavour, ca. 100 calories) and consumed within one to two minutes. After ingesting the samples, subject exhaled through a mouthpiece to collect an end-expiratory breath sample into a 300 mL foil bag at time intervals. Breath samples were taken over a period of 410 min. During this time period, 0.5-1.0 L of water were drunk at a rate of approximately one glass per hour, a light lunch was consumed after 180 min, and physical exercise represented daily routine.

After completion of breath bag collection, analysis was performed by means of a FANci2 breath test analyser based on non-dispersive infrared spectroscopy (Fischer Analysen Instrumente GmbH, Germany). $^{13}$C abundance in breath was expressed as relative difference (0/00) from the universal reference standard (carbon from Pee Dee Belemnite limestone). $^{13}$C enrichment was defined as the difference between $^{13}$C abundance in breath prior to sample ingestion and $^{13}$C abundance at the defined time points after sample ingestion and was given in delta over basal (DOB, % 0/00). From the breath test analyser's operating software (FANci version 2.12.42.14 02/14), values of cumulated percent dose rate (cPDR, corresponding to bioavailability), and the time at half the cPDR value (HLF, corresponding to gastrointestinal half-life) were taken to protocol.

Hard fat (Witepsol®) was from NRC, Germany. Cocoa butter was purchased at a local grocery store. Sodium laurate and lauric acid, microcrystalline cellulose and HPC qualities were from Sigma-Aldrich, USA. HPMC (Metolose® 90SH) was from Harke, Germany, Xanthan (Xantan Texturas) was from Solegraells Guzman, Spain. Carbopol® was from Lubrizol, USA. Glycerolmonooleate and glycerolmonolaurate were from TCI, Belgium.

Several test compositions with particles according to the invention were administered. As shown in the table below, it was found that the particles lead to an increase in bioavailability (test compositions 1, 2, 4, 5 and 6) or to an increased gastrointestinal half-time (test composition 3).

| Sample | Lipid (g) | Polymer (g) | cPDR (%) | HLF (min) |
|---|---|---|---|---|
| Reference 1 | Cocoa butter: 6 g | — | 37 | 219 |
| Reference 2 | Witepsol W25: 6 g | — | 32 | 189 |
| Reference 3 | Witepsol W25: 4 g sodium laurate: 1.25 g | — | 32 | 180 |
| Reference 4 | Witepsol W25: 2 g lauric acid: 2 g | — | 41 | 232 |
| Reference 5 | Prifex 300: 6 g | — | 29.0 | 91.5 |
| Test composition 1 | Cocoa butter: 6 g | Carbopol 971: 2 g | 59 | 222 |
| Test composition 2 | Witepsol W25: 6 g | HPC 1 MDa: 2 g | 53 | 176 |
| Test composition 3 | Witepsol W25: 4 g sodium laurate: 1.25 g | HPC 370 kDa: 1 g | 39 | 243 |
| Test composition 4 | Witepsol W25: 2 g lauric acid: 2 g | HPC 1 MDa: 2 g | 57 | 172 |
| Test composition 5 | Glycerolmonooleate: 3 g, Glycerolmonolaurate: 3 g | HPMC: 1.3 g Xanthan: 0.7 g | 59 | 165 |
| Test composition 6 | Prifex 300: 6 g | Alginex: 3 g Aglupectin HS-RVP: 1 g PromOat: 1 g | 42.1 | 65.2 |

Example 24: In Vitro Mucoadhesion and Particle Integrity Assay

Sodium alginate medium viscosity (alginate #1), alginic acid, sodium laurate and lauric acid, microcrystalline cellulose (MCC), hydroxypropyl-cellulose (HPC) and carboxymethyl-cellulose (CMC) qualities, gum arabic, chitosan and calcium salts were from Sigma-Aldrich, USA. Alginate #3 was from Dragonspice, Germany. Alginate #4 (Satialgine® S 1600) was from Cargill, France. Alginate #5 (Manucol® DH) was from IMCD, Germany. Alginate #6 (Protanal® LF) and alginate #7 (Protanal® PH) were from FMC, UK. Alginate #8 (Alginex® HH) and Alginate #9 (Algin LZ-2) were from Kimica, Japan. Carbopol® qualities were from Lubrizol, USA. Xanthan (Texturas Xantan), gellan gum (Texturas gellan), alginate #2 (Texturas Algin) were from Solegraells Guzman, Spain. HPMC (Metolose® 90SH) was from Harke, Germany. *Psyllium* qualities (99%; 100 Mesh) and guar gum were from Caremoli, Germany. Carob bean gum was from Werz, Germany. Coconut flour was from Noble House, Belgium. Apple pectin, apple pectin low esterified and lysolecithin were from Dragonspice, Germany. Pectin #1 (Pektin Classic AU202) was from Herbstreith & Fox, Germany. Pectin #2 (Aglupectin® HS-RVP) and Tara gum (AgluMix® 01) were from Silva Extracts, Italy. Low methoxyl pectin, amidated low methoxyl pectin, rapid set high methoxyl pectin, and slow set high methoxyl pectin qualities were from Modernist Pantry, USA. Beta-glucan (powder fill of Hafer-Beta glucan Bio Kapseln) was from Raab Vitalfood, Germany. PromOat® beta-glucan was from Tate&Lyle, Sweden. Cocoa powder low fat was from Naturata, Germany. Cocoa powder high fat was from Cebe, Germany. Inulin was from Spinnrad, Germany. Benefiber® resistant dextrin (also known as Benefiber® Nutriose®) was from Novartis, UK.

Witepsol® hard fat qualities were from NRC, Germany. Gelucire® 43/01 hard fat was from Gattefoss6, France. Monoglycerides were from TCI, Belgium. Cocoa butter was purchased at a local super market. Palm fat was from Peter Kölln, Germany. Palm stearin, Omega-3-Concentrate oil and Omega-3-Concentrate powder 67 were from Bressmer, Germany. Palm stearin IP, and palm stearin MB were from Henry Lamotte, Germany. Coconut oil and coconut fat qualities were from Dr. Goerg, Germany. Shea butter #1 was from Gustav Hees, Germany. Shea butter #2 was from Cremer Oleo, Germany. Soy lecithin #1 (powder quality) was from Caelo, Germany. Soy lecithin #2 (Texturas Lecite) was from Solegraells Guzman, Spain. Cocoa mass was from Homborg, Germany. Cera flava and alba beeswax were from Heinrich Klenk, Germany. Conjugated linoleic acid (Tonalin®) was from BASF, Germany. Prifex® 300 palm stearin was from Unimills, The Netherlands. Omega-3 fatty acids (Omega-3 1400) were from Queisser Pharma, Germany. Safflower oil was from Brökelmann, Germany.

Granules were prepared by melting one lipid at 50° C. and optionally adding other lipid components and a few crystals of Oil Red O (Sigma Aldrich, USA) to obtain a homogenous melt or suspension. For test samples polymer(s) were incorporated by mechanical mixing. Each composition was transferred into a zip-loc-bag and cooled to −18° C. in a freezer. The material was first crushed by means of a hammer, shredded to a granulate in a kitchen blender (Bosch Profi-MIXX, Germany), optionally dried under vacuum at 25° C. and then classified through a set of wire mesh sieves (VWR International, Germany) to a granulate size of below 2.0 mm and above 1.3 mm. Fresh pork stomach (from a local butcher) was cut into 3 cm×3 cm pieces and placed into the bottom of a glass petri dish (10 cm diameter). 22 mL fasted-state simulated gastric fluid (FaSSGF) were added to the petri dish. FaSSGF was prepared by dis-solving 1 g of NaCl (Sigma-Aldrich) in 450 mL of water, adding 30 mg of SIF powder (biorelevant.com), adjusting the pH to 2.0 with 0.1 N HCl (Sigma-Aldrich) and adding water to a final volume of 500 mL. The petri dish was covered and placed onto a petri dish shaker (ST5 from CAT, Germany) set to a tilt angle of 12° and a speed of 50/min. The shaker was placed into an oven heated to a temperature of 37° C. After 30 minutes, 350 mg granulate were added to the contents of the petri dish without interrupting agitation. After 5 min, the samples were removed from the oven, and the piece of pork stomach was rinsed three times with water (3 mL each). The material bound to the stomach surface was removed by means of a spatula, transferred into a weighing dish, and dried to constant weight (electronic moisture meter MLB 50-3N, Kern & Sohn, Germany). Dry weight of the mucoadhesive material was recorded and calculated as percent of initial granulate weight, representing binding as a measure of mucoadhesiveness. The petri dish containing the remaining unbound material was agitated at 37° C. for another 15 min, and particle integrity was classified by visual inspection as "low" (complete disintegration or disintegration of at least 50% of the particles), or "high" (disintegration of less than 50% of the particles) or "medium" (disintegration of less than 50% of the particles, but visible loss of small amounts of powders from the particles).

In result, it was found that certain test compositions with particles according to the invention showed a substantially increased binding to the mucosa and/or high particle integrity, as shown in the table below.

| Sample | Lipid (g) | Polymer (g) | Binding | Particle integrity |
|---|---|---|---|---|
| Test 1 | Witepsol W25, 4 g | HPC 1 MDa, 2 g | 75% | high |
| Test 2 | Witepsol W25, 4 g | HPC 1 MDa, 1 g<br>CMC ultra high viscosity, 1 g | 69% | high |
| Test 3 | Witepsol W25, 4 g | CMC ultra high viscosity, 2 g | 53% | high |
| Test 4 | Cocoa butter, 2 g<br>Lauric acid, 2 g | HPC, 1 g<br>CMC, 1 g | 91% | high |
| Test 5 | Cocoa butter, 2 g<br>Glycerolmonolaurate, 2 g | Carbopol 971, 2 g | 92% | high |
| Test 6 | Cocoa butter, 2 g<br>Glycerolmonostearate, 2 g | Carbopol 971, 2 g | 64% | high |
| Test 7 | Cocoa butter, 4 g | HPC, 1 g<br>CMC, 1 g | 35% | n.d. |
| Test 8 | Cocoa butter, 4 g | HPC, 1 g<br>Carbopol 971, 1 g | 69% | high |

-continued

| Sample | Lipid (g) | Polymer (g) | Binding | Particle integrity |
|---|---|---|---|---|
| Test 9 | Cocoa butter, 4 g | Carbopol 971, 2 g | 77% | high |
| Test 10 | Cocoa butter, 2 g<br>Lauric acid, 2 g | Carbopol 971, 2 g | 49% | n.d. |
| Test 11 | Cocoa butter, 4 g | HPC 1 MDa, 2 g | 44% | n.d. |
| Test 12 | Cocoa butter, 2 g<br>Glycerolmonolaurate, 2 g | HPC 1 MDa, 2 g | 55% | n.d. |
| Test 13 | Cocoa butter, 2 g<br>Glycerolmonostearate, 2 g | HPC 1 MDa, 2 g | 84% | high |
| Test 14 | Glycerolmonooleate, 2 g<br>Lauric acid, 2 g | HPMC, 2 g | 50% | n.d. |
| Test 15 | Glycerolmonooleate, 2 g<br>Glycerolmonolaurate, 2 g | HPMC, 2 g | 52% | n.d. |
| Test 16 | Glycerolmonooleate, 2 g<br>Witepsol W25, 2 g | HPMC, 2 g | 67% | high |
| Test 17 | Glycerolmonooleate, 3 g<br>Glycerolmonolaurate, 3 g | Carbopol 971, 2 g | 81% | high |
| Test 18 | Glycerolmonooleate, 3 g<br>Glycerolmonolaurate, 3 g | HPMC, 1.3 g<br>Xanthan, 0.7 g | 72% | high |
| Test 19 | Glycerolmonolaurate, 1.9 g<br>Glycerolmonooleate, 1.1 g<br>Witepsol W25, 1 g | HPMC, 1.9 g<br>Xanthan, 0.1 g | 78% | high |
| Test 20 | Lauric acid, 4 g | HPMC, 1.9 g<br>Xanthan, 0.1 g | 60% | high |
| Test 21 | Lauric acid, 1.9 g<br>Glycerolmonooleate, 1.1 g<br>Witepsol W25, 1 g | HPMC, 1.9 g<br>Xanthan, 0.1 g | 75% | high |
| Test 22 | Lauric acid, 1.9 g<br>Glycerolmonooleate, 1.1 g | HPMC, 1.9 g<br>Xanthan, 0.1 g | 73% | high |
| Test 23 | Glycerolmonooleate, 2.05 g<br>Witepsol W25, 1.95 g | HPMC, 1.9 g<br>Xanthan, 0.1 g | 57% | |
| Test 24 | Glycerolmonolaurate, 1.9 g<br>Glycerolmonooleate, 1.1 g<br>Medium chain triglycerides (MCT), 0.55 g<br>Witepsol W25, 0.45 g | HPMC#2, 1.9 g<br>Xanthan, 0.1 g | 85% | high |
| Test 25 | Glycerolmonolaurate, 1.35 g<br>Glycerolmonooleate, 1.1 g<br>MCT, 0.55 g<br>Witepsol W25, 1 g | Beta-glucan, 1.95 g<br>HPMC, 1.6 g<br>Xanthan, 0.1 g | 68% | high |
| Test 26 | Glycerolmonolaurate, 1.9 g<br>Glycerolmonooleate, 0.6 g<br>Glycerol, 0.5 g<br>Witepsol W25, 1 g | HPMC, 2.4 g<br>Xanthan, 0.1 g | 75% | high |
| Test 27 | Glycerolmonolaurate, 1.35 g<br>Glycerolmonooleate, 1.1 g<br>MCT, 0.55 g<br>Witepsol W25, 1 g | Chitosan, 0.5 g<br>HPMC, 2.5 g<br>Xanthan, 0.1 g | 66% | high |
| Test 28 | Glycerolmonolaurate, 1.35 g<br>Glycerolmonooleate, 1.1 g<br>MCT, 0.55 g<br>Witepsol W25, 1 g | Beta-glucan, 1.9 g<br>HPMC, 2.5 g<br>Xanthan, 0.1 g | 68% | high |
| Test 29 | Glycerolmonolaurate, 1.9 g<br>Glycerolmonooleate, 0.6 g<br>Glycerol, 0.5 g<br>Witepsol W25, 1 g | HPMC, 2.4 g<br>Xanthan, 0.1 g | 75% | high |
| Test 30 | Glycerolmonolaurate, 1.9 g<br>Glycerol, 0.5 g<br>Witepsol W25, 1 g | HPMC, 1.9 g<br>Xanthan, 0.1 g | 43% | high |
| Test 31 | Glycerolmonolaurate, 1.9 g<br>Glycerol, 1 g<br>Witepsol W25, 1 g | HPMC, 2.5 g<br>Xanthan, 0.1 g | 26% | high |
| Test 32 | Glycerolmonolaurate, 1.9 g<br>Glycerolmonooleate, 1.1 g<br>MCT, 0.55 g<br>Witepsol W25, 1 g | HPMC, 3.15 g<br>Xanthan, 0.1 g | 85% | high |
| Test 33 | Glycerolmonolaurate, 1.9 g<br>Imwitor 990, 1.1 g<br>MCT, 0.55 g<br>Witepsol W25, 1 g | HPMC, 3.15 g<br>Xanthan, 0.1 g | 90% | high |
| Test 34 | Glycerolmonolaurate, 1.35 g,<br>Imwitor 990, 1.1 g,<br>MCT, 0.55 g<br>Witepsol W25, 1 g | HPMC, 2.8 g<br>Xanthan, 0.1 g | 81% | high |
| Test 35 | Glycerolmonolaurate, 1.35 g<br>Glycerolmonooleate, 1.1 g | Chitosan, 0.5 g<br>HPMC, 2.5 g | 66% | high |

-continued

| Sample | Lipid (g) | Polymer (g) | Binding | Particle integrity |
|---|---|---|---|---|
| | MCT, 0.55 g | Xanthan, 0.1 g | | |
| | Witepsol W25, 1 g | | | |
| Test 36 | Glycerolmonolaurate, 1.35 g | PromOat, 1.9 g | 61% | high |
| | Glycerolmonooleate, 1.1 g | HPMC, 1.6 g | | |
| | MCT, 0.55 g | Xanthan, 0.1 g | | |
| | Witepsol W25, 1 g | | | |
| Test 37 | Glycerolmonolaurate, 1.35 g | PromOat, 2.5 g | 68% | high |
| | Glycerolmonooleate, 1.1 g | HPMC, 1 g | | |
| | MCT, 0.55 g | Xanthan, 0.5 g | | |
| | Witepsol W25, 1 g | | | |
| Test 38 | Glycerolmonolaurate, 1.95 g | PromOat, 1.5 g | 90% | high |
| | Imwitor 990, 1.6 g | HPMC, 2.75 g | | |
| | MCT, 0.8 g | Xanthan, 0.15 g | | |
| | Witepsol W25, 1.45 g | | | |
| Test 39 | Glycerolmonolaurate, 1.9 g | HPMC, 1.9 g | 83% | high |
| | Imwitor 990, 1.1 g | Xanthan, 0.1 g | | |
| | Witepsol W25, 1 g | | | |
| Test 40 | Glycerolmonolaurate, 3.2 g | PromOat, 1.5 g | 87% | high |
| | Glycerolmonooleate, 1.8 g | HPMC, 2.33 g | | |
| | Witepsol W25, 1.7 g | Xanthan, 0.17 g | | |
| Test 41 | Glycerolmonolaurate, 3.2 g | PromOat, 1.5 g | 65% | high |
| | Imwitor 990, 1.8 g | HPMC, 2.33 g | | |
| | Witepsol W25, 1.7 g | Xanthan, 0.17 g | | |
| Test 42 | Glycerolmonolaurate, 1.9 g | HPMC, 2.5 g | 85% | high |
| | Imwitor 990, 1.1 g | Xanthan, 0.1 g | | |
| | Witepsol W25, 1 g | | | |
| Test 43 | Glycerolmonolaurate, 2.4 g | PromOat, 1.5 g | 86% | high |
| | Glycerolmonooleate, 1.3 g | HPMC, 4 g | | |
| | Witepsol W25, 3.7 g | Xanthan, 0.1 g | | |
| Test 44 | Glycerolmonolaurate, 2.4 g | PromOat, 3 g | 83% | high |
| | Glycerolmonooleate, 1.3 g | HPMC, 3 g | | |
| | Witepsol W25, 3.7 g | Xanthan, 0.1 g | | |
| Test 45 | Glycerolmonolaurate, 1.9 g | HPMC, 1.9 g | 72% | high |
| | Glycerolmonooleate, 1.1 g | Xanthan, 0.1 g | | |
| | Witepsol H35, 1 g | | | |
| Test 46 | Glycerolmonolaurate, 1.6 g | HPMC, 1.9 g | 86% | high |
| | Glycerolmonooleate, 1.4 g | Xanthan, 0.1 g | | |
| | Witepsol H35, 1 g | | | |
| Test 47 | Glycerolmonolaurate, 1.9 g | HPMC, 2.5 g | 87% | high |
| | Glycerolmonooleate, 1.1 g | Xanthan, 0.1 g | | |
| | Witepsol H35, 1 g | | | |
| Test 48 | Glycerolmonolaurate, 2.6 g | PromOat, 1 g | 80% | high |
| | Glycerolmonooleate, 1.4 g | HPMC, 2.9 g | | |
| | Witepsol W25, 4 g | Xanthan, 0.1 g | | |
| Test 49 | Witepsol W25, 4 g | HPMC, 2 g | 47% | high |
| Test 50 | Glycerolmonolaurate, 4 g | HPMC, 2 g | 45% | high |
| Test 51 | Glycerolmonolaurate, 2.6 g | PromOat, 1 g | 65% | high |
| | Glycerolmonooleate, 1.4 g | HPMC, 3 g | | |
| | Witepsol W25, 4 g | | | |
| Test 52 | Glycerolmonolaurate, 1.6 g | HPMC, 1.9 g | 80% | high |
| | | Xanthan, 0.1 g | | |
| Test 53 | Glycerolmonolaurate, 3 g | HPMC, 1.9 g | 83% | high |
| | Witepsol W25, 1 g | Xanthan, 0.1 g | | |
| Test 54 | Glycerolmonolaurate, 2 g | HPMC, 1.9 g | 75% | high |
| | Witepsol W25, 2 g | Xanthan, 0.1 g | | |
| Test 55 | Glycerolmonolaurate, 1 g | HPMC, 1.9 g | 77% | high |
| | Witepsol W25, 3 g | Xanthan, 0.1 g | | |
| Test 56 | Glycerolmonolaurate, 2 g | HPMC, 2.85 g | 78% | high |
| | Witepsol W25, 4 g | Xanthan, 0.15 g | | |
| Test 57 | Glycerolmonolaurate, 4 g | PromOat, 1 g | 80% | high |
| | Witepsol W25, 4 g | HPMC, 2.9 g | | |
| | | Xanthan, 0.1 g | | |
| Test 58 | Glycerolmonolaurate, 3 g | PromOat, 1.125 g | 70% | high |
| | Witepsol W25, 6 g | HPMC, 3.26 g | | |
| | | Xanthan, 0.125 g | | |
| Test 59 | Glycerolmonolaurate, 2 g | PromOat, 1 g | 95% | high |
| | Witepsol W25, 6 g | HPMC, 2.9 g | | |
| | | Xanthan, 0.1 g | | |
| Test 60 | Gelucire 43/01, 1 g | HPMC, 1.9 g | 81% | high |
| | Witepsol W25, 3 g | Xanthan, 0.1 g | | |
| Test 61 | Gelucire 43/01, 2 g | HPMC, 2.85 g | 78% | high |
| | Witepsol W25, 4 g | Xanthan, 0.15 g | | |
| Test 62 | Gelucire 43/01, 3 g | PromOat, 1.125 g | 82% | high |
| | Witepsol W25, 6 g | HPMC, 3.26 g | | |
| | | Xanthan, 0.125 g | | |

-continued

| Sample | Lipid (g) | Polymer (g) | Binding | Particle integrity |
|---|---|---|---|---|
| Test 63 | Gelucire 43/01, 2 g<br>Witepsol W25, 6 g | PromOat, 1 g<br>HPMC, 2.9 g<br>Xanthan, 0.1 g | 78% | high |
| Test 64 | Glycerolmonolaurate, 1 g<br>Witepsol W25, 3 g | HPMC, 2 g | 80% | high |
| Test 65 | Glycerolmonolaurate, 2 g<br>Witepsol W25, 6 g | PromOat, 1 g<br>HPMC, 3 g | 82% | high |
| Test 66 | Glycerolmonolaurate, 2 g<br>Witepsol W25, 6 g | Psyllium (99%; 100 Mesh), 3 g<br>HPMC, 1 g | 93% | high |
| Test 67 | Glycerolmonolaurate, 2 g<br>Witepsol W25, 1 g<br>Shea butter, 5 g | Psyllium (99%; 100 Mesh), 3 g<br>HPMC, 1 g | 85% | high |
| Test 68 | Glycerolmonolaurate, 2 g<br>Witepsol W25, 2 g<br>Shea butter, 4 g | Psyllium (99%; 100 Mesh), 3 g<br>HPMC, 1 g | 60% | high |
| Test 69 | Glycerolmonolaurate, 2 g<br>Witepsol W25, 6 g | PromOat, 1 g<br>Apple pectin, 1 g<br>HPMC, 2 g | 90% | high |
| Test 70 | Glycerolmonolaurate, 2 g<br>Witepsol W25, 6 g | PromOat, 1 g<br>Apple pectin, 1 g<br>HPMC, 1.9 g<br>Xanthan, 0.1 g | 55% | high |
| Test 71 | Glycerolmonolaurate, 2 g<br>Witepsol W25, 6 g | PromOat, 0.5 g<br>Apple pectin, 0.5 g<br>HPMC, 3 g | 80% | high |
| Test 72 | Glycerolmonolaurate, 2 g<br>Witepsol W25, 6 g | PromOat, 0.5 g<br>Apple pectin, 1.5 g<br>HPMC, 2 g | 65% | high |
| Test 73 | Glycerolmonolaurate, 2 g<br>Witepsol W25, 6 g | PromOat, 1.5 g<br>Apple pectin, 1.5 g<br>HPMC, 1 g | 50% | medium |
| Test 74 | Witepsol W25, 2 g | HPMC, 2 g<br>Cocoa powder (high-fat), 2 g | 88% | high |
| Test 75 | Glycerolmonolaurate, 2 g<br>Witepsol W25, 4 g | HPMC, 3 g<br>Cocoa powder (high-fat), 4 g | 85% | high |
| Test 76 | Glycerolmonolaurate, 2 g<br>Witepsol W25, 4 g | PromOat, 1 g<br>HPMC, 2 g<br>Cocoa powder (high-fat), 4 g | 45% | medium |
| Test 77 | Gelucire 43/01, 2 g<br>Witepsol W25, 4 g | HPMC, 4 g<br>Cocoa powder (high-fat), 4 g | 89% | high |
| Test 78 | Gelucire 43/01, 2 g<br>Witepsol W25, 4 g | Apple pectin, 1 g<br>HPMC, 3 g<br>Cocoa powder (high-fat), 4 g | 77% | high |
| Test 79 | Gelucire 43/01, 2 g<br>Witepsol W25, 4 g | HPMC, 4 g<br>Cocoa powder (low-fat), 4 g | 90% | high |
| Test 80 | Gelucire 43/01, 2 g<br>Witepsol W25, 4 g | HPMC, 3 g<br>Xanthan, 1 g<br>Cocoa powder (low-fat), 4 g | 70% | high |
| Test 81 | Gelucire 43/01, 2 g<br>Witepsol W25, 4 g | Psyllium (99%; 100 Mesh), 2 g<br>HPMC, 2 g<br>Cocoa powder (low-fat), 4 g | 75% | high |
| Test 82 | Gelucire 43/01, 2 g<br>Witepsol W25, 4 g | Psyllium (99%; 100 Mesh), 1 g<br>HPMC, 2 g<br>Xanthan, 1 g<br>Cocoa powder (low-fat), 4 g | 25% | high |
| Test 83 | Gelucire 43/01, 2 g<br>Witepsol W25, 3.5 g<br>Glycerolmonooleate, 0.5 g | HPMC, 3.8 g<br>Xanthan, 0.2 g<br>Cocoa powder (low-fat), 4 g | 85% | high |
| Test 84 | Gelucire 43/01, 2 g<br>Witepsol W25, 4 g | Alginate 1, 2 g<br>HPMC, 2 g<br>Cocoa powder (low-fat), 4 g | 57% | high |
| Test 85 | Gelucire 43/01, 2 g<br>Witepsol W25, 4 g<br>Palm fat, 2 g | PromOat, 0.5 g<br>HPMC, 3.5 g<br>Cocoa powder (low-fat), 0.5 g | 71% | high |
| Test 86 | Gelucire 43/01, 2 g<br>Witepsol W25, 4 g<br>Palm fat, 2 g | PromOat, 0.5 g<br>HPMC, 3.3 g<br>Xanthan, 0.2 | 72% | high |
| Test 87 | Gelucire 43/01, 6 g<br>Palm fat, 2 g | PromOat, 0.5 g<br>HPMC, 3.4 g<br>Xanthan, 0.1 | 92% | high |
| Test 88 | Glycerolmonolaurate, 1 g<br>Witepsol W25, 3 g | Alginate#1, 1 g<br>HPMC, 1 g | 88% | high |

-continued

| Sample | Lipid (g) | Polymer (g) | Binding | Particle integrity |
|---|---|---|---|---|
| Test 89 | Glycerolmonolaurate, 1.33 g<br>Witepsol W25, 1.33 g<br>Coco fat, 1.33 g | Alginate#1, 1 g<br>HPMC, 1 g | 60% | high |
| Test 90 | Glycerolmonolaurate, 1.33 g<br>Witepsol W25, 1.33 g<br>Coco oil, 1.33 g | Alginate#1, 1 g<br>HPMC, 1 g | 80% | high |
| Test 91 | Glycerolmonolaurate, 1.33 g<br>Witepsol W25, 1.33 g<br>Coco oil, 1.33 g | Alginate#1, 1 g<br>HPMC, 1 g<br>Cocoa powder (strong de-oiled), 1 g | 84% | high |
| Test 92 | Glycerolmonolaurate, 1.33 g<br>Witepsol W25, 1.33 g<br>Coco oil, 1.33 g | Alginate#1, 1 g<br>HPMC, 1 g<br>Calcium L-lactate hydrate, 0.006 g | 86% | high |
| Test 93 | Glycerolmonolaurate, 1.33 g<br>Witepsol W25, 1.33 g<br>Coco oil, 1.33 g | Alginate#1, 1 g<br>HPMC, 1 g<br>Calcium L-lactate hydrate, 0.06 g | 60% | high |
| Test 94 | Glycerolmonolaurate, 1.33 g<br>Witepsol W25, 1.33 g<br>Coco oil, 1.33 g | Alginate#1, 1 g<br>HPMC, 1 g<br>Calcium L-lactate hydrate, 0.6 g | 49% | high |
| Test 95 | Glycerolmonolaurate, 2.67 g<br>Witepsol W25, 1.67 g<br>Coco oil, 1.67 g<br>Cocoa mass, 4 g | Alginate#1, 1 g<br>HPMC, 1 g | 60% | high |
| Test 96 | Glycerolmonolaurate, 1 g<br>Witepsol W25, 3 g | Alginate#2, 1 g<br>HPMC, 1 g | 92% | high |
| Test 97 | Glycerolmonolaurate, 1 g<br>Witepsol W25, 3 g | Alginate#2, 1 g<br>HPMC, 1 g<br>Calcium L-lactate hydrate, 0.006 g | 62% | high |
| Test 98 | Glycerolmonolaurate, 1 g<br>Witepsol W25, 2.5 g<br>Coco oil, 0.5 g | HPMC, 2 g | 80% | high |
| Test 99 | Witepsol W25, 4 g | HPC 1.15 MDa, 2 g | 92% | high |
| Test 100 | Witepsol W25, 4 g | HPC 0.85 MDa, 2 g | 92% | high |
| Test 101 | Glycerolmonolaurate, 1 g<br>Witepsol W25, 3 g | Low methoxyl pectin, 2 g | 45% | medium |
| Test 102 | Glycerolmonolaurate, 1 g<br>Witepsol W25, 3 g | Amidated low methoxyl pectin, 2 g | 74% | high |
| Test 103 | Glycerolmonolaurate, 1 g<br>Witepsol W25, 3 g | Rapid set high methoxyl pectin, 2 g | 62% | high |
| Test 104 | Glycerolmonolaurate, 1 g<br>Witepsol W25, 3 g | Slow set high methoxyl pectin, 2 g | 81% | high |
| Test 105 | Glycerolmonolaurate, 1 g<br>Witepsol W25, 3 g | Slow set high methoxyl pectin, 4 g | 85% | high |
| Test 106 | Glycerolmonolaurate, 1 g<br>Witepsol W25, 3 g | Apple pectin, 2 g | 66% | high |
| Test 107 | Glycerolmonolaurate, 1 g<br>Witepsol W25, 3 g | Apple pectin, 4 g | 90% | high |
| Test 108 | Glycerolmonolaurate, 2 g<br>Witepsol W25, 4 g | Apple pectin, 3 g | 70% | high |
| Test 109 | Glycerolmonolaurate, 2 g<br>Witepsol W25, 4 g | Apple pectin, 4 g | 86% | high |
| Test 1102 | Glycerolmonolaurate, 1 g<br>Witepsol W25, 3 g | Xanthan, 2 g | 73% | high |
| Test 111 | Glycerolmonolaurate, 1 g<br>Witepsol W25, 3 g | Xanthan, 1 g | 65% | high |
| Test 112 | Glycerolmonolaurate, 1 g<br>Witepsol W25, 3 g | Carob bean gum, 2 g | 46% | medium |
| Test 113 | Glycerolmonolaurate, 1 g<br>Witepsol W25, 3 g | PromOat, 1 g<br>Xanthan, 1 g | 63% | high |
| Test 114 | Glycerolmonolaurate, 1 g<br>Witepsol W25, 3 g | Psyllium (95%; 40 Mesh), 3 g | 68% | high |
| Test 115 | Glycerolmonolaurate, 1 g<br>Witepsol W25, 3 g | Psyllium (98%; 100 Mesh), 3 g | 46% | medium |
| Test 116 | Glycerolmonolaurate, 1 g<br>Witepsol W25, 3 g | Psyllium (99%; 100 Mesh), 3 g | 85% | high |
| Test 117 | Glycerolmonolaurate, 1 g<br>Witepsol W25, 3 g | Psyllium (99%; 100 Mesh Plus), 3 g | 70% | high |
| Test 118 | Glycerolmonolaurate, 1 g<br>Witepsol W25, 3 g | Psyllium (99%; 100 Mesh), 2 g | 52% | medium |
| Test 119 | Glycerolmonolaurate, 1 g<br>Witocan H, 3 g | Psyllium (99%; 100 Mesh), 3 g | 70% | high |

-continued

| Sample | Lipid (g) | Polymer (g) | Binding | Particle integrity |
|---|---|---|---|---|
| Test 120 | Glycerolmonolaurate, 1 g<br>Witocan P, 3 g | Psyllium (99%; 100 Mesh), 3 g | 60% | high |
| Test 121 | Glycerolmonolaurate, 2 g<br>Shea butter 1.2 g | Psyllium (99%; 100 Mesh), 3 g | 50% | medium |
| Test 122 | Glycerolmonolaurate, 2 g<br>Shea butter 2.2 g | Psyllium (99%; 100 Mesh), 3 g | 42% | medium |
| Test 123 | Glycerolmonolaurate, 1 g<br>Witepsol W25, 3 g | Guar gum (200 Mesh), 2 g | 26% | low |
| Test 124 | Glycerolmonolaurate, 1 g<br>Witepsol W25, 3 g | Carbopol 971, 2 g | 84% | high |
| Test 125 | Glycerolmonolaurate, 1 g<br>Witepsol W25, 3 g | Alginic acid, 2 g | 15% | low |
| Test 126 | Glycerolmonolaurate, 1 g<br>Witepsol W25, 3 g | Alginate#2, 2 g | 86% | high |
| Test 127 | Glycerolmonolaurate, 1 g<br>Witepsol W25, 3 g | Alginate#2, 1 g<br>Apple pectin, 1 g | 95% | high |
| Test 128 | Glycerolmonolaurate, 1 g<br>Witepsol W25, 3 g | Alginate#2, 1 g<br>Prickly pear pectin, 1 g | 80% | high |
| Test 129 | Cera flava, 3.2 g<br>Coco oil, 4.8 g | Alginate#2, 2 g<br>Apple pectin, 2 g | 85% | high |
| Test 130 | Cera alba, 3.2 g<br>Coco oil, 4.8 g | Alginate#2, 2 g<br>Apple pectin, 2 g | 84% | high |
| Test 131 | Gelucire 43/01, 6 g<br>Coco oil, 2 g | Alginate#2, 2 g<br>Apple pectin, 1.9 g<br>Konjac flour, 0.1 g | 59% | high |
| Test 132 | Gelucire 43/01, 6 g<br>Coco oil, 2 g | Alginate#2, 2 g<br>Apple pectin, 1.9 g<br>Xanthan, 0.1 g | 75% | high |
| Test 133 | Glycerolmonolaurate, 1 g<br>Witepsol W25, 3 g | Alginate#3, 2 g | 75% | high |
| Test 134 | Glycerolmonolaurate, 1 g<br>Witepsol W25, 3 g | Alginate#2, 2 g<br>Amidated low methoxyl pectin, 2 g | 68% | high |
| Test 135 | Glycerolmonolaurate, 1 g<br>Witepsol W25, 3 g | Alginate#2, 2 g<br>Low methoxyl pectin, 2 g | 75% | high |
| Test 136 | Glycerolmonolaurate, 1 g<br>Witepsol W25, 3 g | Alginate#2, 2 g<br>Slow set high methoxyl pectin, 2 g | 65% | high |
| Test 137 | Glycerolmonolaurate, 1 g<br>Witepsol W25, 3 g | Alginate#2, 2 g<br>Rapid set high methoxyl pectin, 2 g | 78% | high |
| Test 138 | Gelucire 43/01, 4 g<br>Coco oil, 2 g<br>Soy lecithin #1, 2 g | Alginate#2, 2 g<br>Apple pectin, 2 g | 91% | high |
| Test 139 | Gelucire 43/01, 5 g<br>Coco oil, 2 g<br>Soy lecithin #1, 1 g | Alginate#2, 2 g<br>Apple pectin, 2 g | 92% | high |
| Test 140 | Gelucire 43/01, 5 g<br>Coco oil, 2 g<br>Soy lecithin #2, 1 g | Alginate#2, 2 g<br>Apple pectin, 2 g | 86% | high |
| Test 141 | Witocan P, 4 g | MCC, 2 g | <2% | low |
| Test 142 | Witepsol W25, 4 g | MCC, 2 g | <2% | low |
| Test 143 | Palm stearin, 7 g<br>Soy lecithin #1, 1 g | Alginate#2, 2 g<br>Apple pectin, 2 g | 93% | high |
| Test 144 | Palm stearin, 8 g | Alginate#2, 2 g<br>Apple pectin, 2 g<br>PromOat, 2 g<br>Cocoa powder (low fat), 2 g | 70% | high |
| Test 145 | Palm stearin, 8 g | Alginate#2, 2 g<br>Apple pectin, 2 g | 55% | high |
| Test 146 | Palm stearin, 7 g<br>Soy lecithin #1, 1 g | Alginate#2, 2 g<br>Apple pectin, 2 g<br>PromOat, 2 g | 56% | high |
| Test 147 | Palm stearin, 7 g<br>Soy lecithin #1, 1 g | Alginate#2, 2 g<br>Apple pectin, 2 g<br>Cocoa powder (low fat), 2 g | 48% | high |
| Test 148 | Palm stearin, 7 g<br>Soy lecithin #1, 1 g | Alginate#2, 2 g<br>Apple pectin, 2 g<br>Psyllium, 2 g | 50% | high |
| Test 149 | Palm stearin, 7 g<br>Soy lecithin #1, 1 g | Alginate#2, 2 g<br>Apple pectin, 2 g<br>Coco flour, 2 g | 62% | high |
| Test 150 | Palm stearin, 7 g<br>Soy lecithin #1, 1 g | Alginate#2, 4 g<br>Apple pectin, 4 g | 70% | high |
| Test 151 | Glycerolmonolaurate, 4 g<br>Coco oil, 4 g | Alginate#2, 2 g<br>Apple pectin, 2 g | 65% | high |

-continued

| Sample | Lipid (g) | Polymer (g) | Binding | Particle integrity |
|---|---|---|---|---|
| Test 152 | Glycerolmonolaurate, 3 g<br>Palm stearin, 1 g<br>Coco oil, 4 g | Alginate#2, 2 g<br>Apple pectin, 2 g | 65% | high |
| Test 153 | Glycerolmonolaurate, 2.67 g<br>Palm stearin, 2.67 g<br>Coco oil, 2.67 g | Alginate#2, 2 g<br>Apple pectin, 2 g | 67% | high |
| Test 154 | Glycerolmonolaurate, 3.5 g<br>Coco oil, 3.5 g<br>Soy lecithin #2, 1 g | Alginate#2, 2 g<br>Apple pectin, 2 g | 87% | high |
| Test 155 | Glycerolmonolaurate, 3 g<br>Palm stearin, 1 g<br>Coco oil, 3 g<br>Soy lecithin #2, 1 g | Alginate#2, 2 g<br>Apple pectin, 2 g | 92% | high |
| Test 156 | Palm stearin, 7 g<br>Soy lecithin #1, 1 g | Alginate#2, 4 g | 65% | high |
| Test 157 | Palm stearin, 7 g<br>Soy lecithin #1, 1 g | Alginate#2, 2 g<br>Apple pectin, 2 g<br>Gum arabic, 1 g | 84% | high |
| Test 1598 | Palm stearin, 7 g<br>Soy lecithin #1, 1 g | Alginate#2, 2.7 g<br>Apple pectin, 1.3 g | 91% | high |
| Test 159 | Palm stearin, 7 g<br>Soy lecithin #1, 1 g | Alginate#2, 1.3 g<br>Apple pectin, 2.7 g | 50% | high |
| Test 160 | Palm stearin, 6 g<br>Cera flava, 1 g<br>Soy lecithin #1, 1 g | Alginate#2, 2 g<br>Apple pectin, 2 g | 83% | high |
| Test 161 | Palm stearin, 7 g<br>Soy lecithin #1, 1 g | Alginate#2, 2.7 g<br>Apple pectin, 1.3 g<br>Calcium carbonate, 0.012 g | 85% | high |
| Test 162 | Palm stearin, 7 g<br>Soy lecithin #1, 1 g | Alginate#2, 2.7 g<br>Apple pectin, 1.3 g<br>Calcium carbonate, 0.12 g | 77% | high |
| Test 163 | Palm stearin MB, 7 g<br>Soy lecithin #1, 1 g | Alginate#2, 2.7 g<br>Apple pectin, 1.3 g | 69% | high |
| Test 164 | Palm stearin IP, 7 g<br>Soy lecithin #1, 1 g | Alginate#2, 2.7 g<br>Apple pectin, 1.3 g | 45% | high |
| Test 165 | Palm stearin, 7 g<br>Soy lecithin #2, 1 g | Alginate#2, 2.7 g<br>Apple pectin, 1.3 g | 92% | high |
| Test 166 | Palm stearin, 7.5 g<br>Soy lecithin #2, 0.5 g | Alginate#2, 2.7 g<br>Apple pectin, 1.3 g | 63% | high |
| Test 167 | Palm stearin, 6.5 g<br>Soy lecithin #2, 1.5 g | Alginate#2, 2.7 g<br>Apple pectin, 1.3 g | 70% | high |
| Test 168 | Palm stearin, 6.5 g<br>Soy lecithin #1, 1.5 g | Alginate#2, 2.7 g<br>Apple pectin, 1.3 g<br>Inulin, 1 g | 80% | high |
| Test 169 | Palm stearin, 6.5 g<br>Soy lecithin #1, 1.5 g | Alginate#2, 2.7 g<br>Apple pectin (low esterified), 1.3 g | 65% | high |
| Test 170 | Palm stearin, 7 g<br>Lysolecithin 1, 1 g | Alginate#2, 2.7 g<br>Apple pectin, 1.3 g | 70% | high |
| Test 171 | Palm stearin, 4 g<br>Soy lecithin #2, 1 g | Alginate#2, 10 g | 75% | high |
| Test 172 | Palm stearin, 6.5 g<br>Soy lecithin #2, 1 g | Alginate#2, 7.5 g | 85% | high |
| Test 173 | Palm stearin, 6.5 g<br>Soy lecithin #2, 1 g | Alginate#2, 5 g<br>Apple pectin, 2.5 g | 70% | high |
| Test 174 | Palm stearin, 6.5 g<br>Soy lecithin #2, 1 g | Alginate#2, 3.75 g<br>Apple pectin, 3.75 g | 59% | high |
| Test 175 | Palm stearin, 6.5 g<br>Soy lecithin #2, 1 g | Alginate#4, 7.5 g | 80% | high |
| Test 176 | Palm stearin, 6.5 g<br>Soy lecithin #2, 1 g | Alginate#4, 5 g<br>Apple pectin, 2.5 g | 82% | high |
| Test 177 | Palm stearin, 6.5 g<br>Soy lecithin #2, 1 g | Alginate#4, 3.75 g<br>Apple pectin, 3.75 g | 82% | high |
| Test 178 | Palm stearin, 7.5 g | Alginate#4, 7.5 g | 60% | high |
| Test 179 | Palm stearin, 4 g<br>Soy lecithin #2, 1 g | Alginate#4, 10 g | 76% | high |
| Test 180 | Palm stearin, 4 g<br>Soy lecithin #2, 1 g | Alginate#4, 7.5 g | 85% | high |
| Test 181 | Palm stearin, 6.5 g<br>Soy lecithin #2, 1 g | Alginate#4, 3.75 g<br>Pectin#1, 3.75 g | 73% | high |
| Test 182 | Palm stearin, 5 g | Alginate#4, 7.5 g | 73% | high |
| Test 183 | Palm stearin, 4.75 g<br>Soy lecithin #2, 0.25 g | Alginate#4, 7.5 g | 74% | high |
| Test 184 | Palm stearin, 4.5 g<br>Soy lecithin #2, 0.5 g | Alginate#4, 7.5 g | 79% | high |
| Test 185 | Palm stearin, 5 g | Alginate#5, 7.5 g | 68% | high |

-continued

| Sample | Lipid (g) | Polymer (g) | Binding | Particle integrity |
|---|---|---|---|---|
| Test 186 | Palm stearin, 5 g | Alginate#6, 7.5 g | 51% | high |
| Test 187 | Palm stearin, 5 g | Alginate#7, 7.5 g | 32% | |
| Test 188 | Palm stearin, 5 g | Alginate#8, 7.5 g | 72% | high |
| Test 189 | Palm stearin, 5 g | Alginate#9, 7.5 g | 31% | high |
| Test 190 | Palm stearin, 8 g | Alginate#7, 4 g | 19% | medium |
| Test 191 | Palm stearin, 8 g | Alginate#8, 4 g | 73% | high |
| Test 192 | Palm stearin, 8 g | Alginate#9, 4 g | 13% | medium |
| Test 193 | Palm stearin, 7.5 g | Alginate#8, 5 g | 75% | yes |
| Test 194 | Palm stearin, 6 g | Alginate#8, 6 g | 78% | no |
| Test 195 | Palm stearin, 6 g | Alginate#8, 5 g<br>Pectin#1, 1 g | 76% | yes |
| Test 196 | Palm stearin, 6 g | Alginate#8, 5 g<br>Pectin#2, 1 g | 82% | high |
| Test 197 | Palm stearin, 6 g | Alginate#4, 5 g<br>Pectin#2, 1 g | 82% | high |
| Test 198 | Palm stearin, 6 g | Alginate#4, 5 g<br>Pectin#2, 1 g<br>PromOat, 1 g | 75% | high |
| Test 199 | Palm stearin, 6 g | Alginate#4, 5 g<br>Pectin#2, 1 g<br>PromOat, 0.5 g | 83% | high |
| Test 200 | Palm stearin, 6 g | Alginate#4, 4 g<br>Pectin#2, 1 g<br>PromOat, 1 g | 85% | high |
| Test 201 | Palm stearin, 6 g | Alginate#4, 5 g<br>PromOat, 1 g | 91% | high |
| Test 202 | Palm stearin, 6 g | Alginate#4, 4 g<br>PromOat, 2 g | 84% | high |
| Test 203 | Palm stearin, 7 g | Alginate#4, 3 g<br>Pectin#2, 1 g<br>PromOat, 1 g | 92% | high |
| Test 204 | Palm stearin, 7 g | Alginate#8, 3 g<br>Pectin 2, 1 g<br>PromOat, 1 g | 94% | high |
| Test 205 | Palm stearin, 6.5 g<br>Conjugated linoleic acid, 0.5 g | Alginate#4, 3 g<br>Pectin#2, 1 g<br>PromOat, 1 g | 73% | high |
| Test 206 | Palm stearin, 6 g<br>Conjugated linoleic acid, 1 g | Alginate#4, 3 g<br>Pectin#2, 1 g<br>PromOat, 1 g | 73% | high |
| Test 207 | Glycerolmonolaurate, 1 g<br>Witepsol W25, 2.5 g<br>Conjugated linoleic acid, 0.5 g | HPMC, 2 g | 83% | high |
| Test 208 | Palm stearin, 7 g | Alginate#4, 3 g<br>Apple pectin, 1 g<br>PromOat, 1 g | 89% | high |
| Test 209 | Palm stearin, 5 g | Alginate#4, 3 g<br>Apple pectin, 1 g<br>PromOat, 1 g | 87% | high |
| Test 210 | Palm stearin, 5 g | Alginate#4, 3 g<br>Pectin 2, 1 g<br>PromOat, 1 g | 89% | high |
| Test 211 | Palm stearin, 5.5 g | Alginate#4, 3 g<br>Apple pectin, 1 g<br>PromOat, 1 g | 89% | high |
| Test 212 | Palm stearin, 6 g | Alginate#4, 3 g<br>Apple pectin, 1 g<br>PromOat, 1 g | 89% | high |
| Test 213 | Palm stearin, 6 g, 3.8 g<br>Omega-3 fatty acid 1, 1.2 g | Alginate#4, 3 g<br>Apple pectin, 1 g<br>PromOat, 1 g | 92% | high |
| Test 214 | Prifex 300, 5.5 g | Alginate#4, 3 g<br>Apple pectin, 1 g<br>PromOat, 1 g | 86% | high |
| Test 215 | Prifex 300, 5.5 g | Alginate#4, 3 g<br>Pectin 2, 1 g<br>PromOat, 1 g | 87% | high |
| Test 216 | Palm stearin, 5.5 g | Alginate#4, 3 g<br>Benefiber, 2 g | 76% | high |
| Test 217 | Palm stearin, 5.5 g | Alginate#4, 3 g<br>Pectin 2, 1 g<br>Benefiber, 1 g | 81% | high |
| Test 218 | Palm stearin, 5.5 g | Alginate#4, 1 g<br>Benefiber, 4 g | 63% | high |

-continued

| Sample | Lipid (g) | Polymer (g) | Binding | Particle integrity |
|---|---|---|---|---|
| Test 219 | Palm stearin, 5.5 g | Alginate#4, 2 g<br>Benefiber, 3 g | 82% | high |
| Test 220 | Palm stearin, 5.5 g | Alginate#4, 2.5 g<br>Benefiber, 2.5 g | 78% | high |
| Test 221 | Palm stearin, 5.5 g | Alginate#4, 2 g<br>Benefiber, 3 g | 82% | high |
| Test 222 | Palm stearin, 5.5 g | Alginate#4, 2.5 g<br>Benefiber, 2.5 g | 78% | high |
| Test 223 | Palm stearin, 5 g | Tara gum, 5 g | 62% | high |
| Test 224 | Palm stearin, 5 g | Gum arabic, 5 g | n.d. | high |
| Test 225 | Palm stearin, 5 g | Pectin 2, 1 g<br>Benefiber, 2 g<br>PromOat, 2 g | n.d. | medium |
| Test 226 | Palm stearin, 5 g | Pectin 2, 1 g<br>Benefiber, 2.5 g<br>PromOat, 1.5 g | n.d. | medium |
| Test 227 | Prifex 300, 3.5 g<br>Safflower oil, 2 g<br>Omega-3 oil, 0.5 g | Alginate 8, 3 g<br>Pectin 2, 1 g<br>Benefiber, 2 g | 86% | high |
| Test 228 | Prifex 300, 3.5 g<br>Safflower oil, 2 g<br>Omega-3 oil, 0.5 g | Alginate 4, 3 g<br>Pectin 2, 1 g<br>Benefiber, 2 g | 77% | high |
| Test 229 | Prifex 300, 3.5 g<br>Safflower oil, 2 g<br>Omega-3 oil, 0.5 g | Alginate 8, 3 g<br>Pectin 2, 1 g<br>Benefiber, 3 g | 60% | high |
| Test 230 | Prifex 300, 3.5 g<br>Safflower oil, 2 g<br>Omega-3 oil, 0.5 g | Alginate 8, 3 g<br>Pectin 2, 1 g<br>Benefiber, 3 g<br>PromOat, 1.5 g | 71% | high |
| Test 231 | Prifex 300, 3.5 g<br>Safflower oil, 2 g<br>Omega-3 oil, 0.5 g | Alginate 8, 3 g<br>Pectin 2, 1 g<br>Nutriose FB, 2 g | 83% | high |
| Test 232 | Prifex 300, 3.5 g<br>Safflower oil, 2 g<br>Omega-3 oil, 0.5 g | Alginate 8, 3 g<br>Pectin 2, 1 g<br>Nutriose FM, 2 g | 82% | high |
| Test 233 | Prifex 300, 9 g<br>Linseed oil, 1 g | Alginate 8, 3 g<br>Pectin 2, 1 g<br>PromOat, 1 g<br>Benefiber, 5 g | 60% | high |
| Test 234 | Prifex 300, 5.5 g | Alginex, 3 g<br>Aglupectin HS-RVP, 1 g<br>PromOat 1 g | 83% | high |

Example 25: Preparation of a Premix by High-Shear Granulation 4.5 kg of hard fat (Witepsol® W25, Cremer Oleo), 1.5 kg of glycerol monolaurate (Mosselman, Belgium), and 3.0 kg HPMC (Metolose 60SH, Shin Etsu, Japan) were introduced into a Ploughshare mixer (Lödige, Germany) equipped with a heating jacket. Under continuous mixing operation at 80 rpm, the temperature in the vessel was raised to 60° C. and until the lipid components were completely molten. With continued mixing, heating was stopped and 2 kg of crushed dry ice were added within 5 min. The resulting granulate was removed from the vessel after evaporation of the carbon dioxide used as premix for extrusion experiments. Where considered expedient, the resulting granulate particles were dried under vacuum at 25° C. to remove residual condensed water; e.g. prior to classifying them.

Example 26: Preparation of a Premix by High-Shear Granulation 3.0 kg of hard fat (Witepsol® W25, Cremer Oleo), 1.0 kg of glycerol monolaurate (Mosselman, Belgium) were introduced into a Ploughshare mixer (Lödige, Germany) equipped with a heating jacket. Under continuous mixing operation at 80 rpm, the temperature in the vessel was raised to 60° C. and until the lipid components were completely molten. With continued mixing, heating was stopped and 3.0 kg of psyllium seed husks (Carepsyllium, Caremoli, Germany) were added and after 5 min, 2 kg of crushed dry ice were added within 5 min. The resulting granulate was removed from the vessel after evaporation of the carbon dioxide and used as premix for extrusion experiment 29. Where considered expedient, the resulting granulate particles were dried under vacuum at 25° C. to remove residual condensed water; e.g. prior to classifying them.

Example 27: Preparation of a Granulate by High-Shear Granulation 750 g of hard fat (Witepsol® W25, Cremer Oleo), 250 g of glycerol monolaurate (Mosselman, Belgium), and 500 g HPMC (Metolose® 60SH, Shin Etsu, Japan) were introduced into a Ploughshare mixer (Lödige, Germany) equipped with a heating jacket. Under continuous mixing operation at 200 rpm, the temperature in the vessel was raised to 54° C. and until the lipid components were completely molten. With continued mixing, heating was stopped and 1 kg of crushed dry ice was added within 5 min. The resulting granulate was removed from the vessel, optionally dried under vacuum at 25° C. and passed through a set of wire mesh sieves (1.0 mm (mesh 18) and 2.0 mm (mesh 10)

and 3.15 mm, VWR, Germany) to give the product. 51% (w/w) of the material were obtained as particle size fraction of 1.0-3.15 mm.

Example 28: Preparation of a Granulate by High-Shear Granulation 900 g alginate (Satialgine®, Cargill, Germany), 60 g soy lecithin (powder quality, Golden Peanut, Germany) and 540 g of palm stearin (Palm Stearin 54, Bressmer, Germany) were introduced into a Ploughshare mixer (Lödige, Germany) equipped with a heating jacket. Under continuous mixing operation at 200 rpm, the temperature in the vessel was raised to 60° C. and until the lipid components were completely molten. With continued mixing, heating was stopped and 440 g of crushed dry ice were added within 5 min. The resulting granulate was removed from the vessel, optionally dried under vacuum at 25° C. and passed through a set of wire mesh sieves (1.0 mm (mesh 18) and 2.0 mm (mesh 10) and 3.15 mm, VWR, Germany) to give the product. 48% (w/w) of the material were obtained as particle size fraction of 1.0-3.15 mm.

Example 29: Preparation of Particles by Extrusion

A premix prepared according to the protocol of experiment 26, comprising 300 g hard fat (Witepsol® W25, Cremer Oleo, Germany), 100 g glycerol monolaurate (Mosselman, Belgium) and 300 g psyllium seed husks (Carepsyllium, Caremoli, Germany), was fed via a volumetric dosing system (Dosimex DO-50, Gabler, Germany) into a powder inlet of a twin screw extruder (Extruder DE-40/10, Gabler, Germany) and extruded at a temperature range of 30-35° C. to strands of 1.0 mm diameter. Extruded strands were cut to granules by means of rotating blades. Granules were subsequently rounded in a spheroniser (Spheronizer 250, Gabler, Germany) to particles of ca. 1 mm diameter.

Example 30: Preparation of Particles by Extrusion

A molten premix of 187.5 g hard fat (Witepsol® W25, Cremer Oleo, Germany), 356.25 g glycerol monolaurate (Mosselman, Belgium) and 206.25 g glycerol monooleate (Mosselman, Belgium) was prepared in a beaker on a hot plate (at 80° C.) equipped with an overhead stirrer and was fed by means of a peristaltic pump (Masterflex®, Thermo Fisher, Germany) to one inlet opening of a twin screw extruder (Pharma 11 HME, Thermo Fisher, Germany). In parallel, a powder premix of 256.25 g HPMC (Metolose® 60SH, Shin Etsu, Japan) and 18.75 g xanthan (Xanthan F F, Jungbunzlauer, Switzerland) were fed via volumetric dosing system (Volumetric Single Screw Feeder, Thermo Fisher, Germany) to the powder inlet opening of the extruder, and the mixture was extruded at a temperature range of 30-35° C. to strands of 1.5 mm diameter and subsequently broken and rounded in a spheroniser (Caleva MBS 120, Thermo Fisher, Germany) to a granulate of ca. 1-2 mm.

Example 31: Coating of Cores with a Mixture of Lipid and Emulsifier 600 g granulate prepared according to one of examples 27-30 were loaded into fluid bed device (Ventilus V-2.5/1, Innojet, Germany, equipped with an IPC3 product reservoir) and fluidised at a bed temperature of 20° C. at an air flow of 90 cubic meters/h. 105.0 g Dynasan® 115 and 45.0 g Polysorbate 65 were molten in a beaker on a hot plate (at 80° C.) equipped with an overhead stirrer. The hot melt was sprayed onto the granulate using a peristaltic pump and a top spraying procedure at a spray rate of 6.5 g/min. Samples of different amounts of coating were taken at time intervals, corresponding to 10, 15, 20, and 25% (w/w).

Example 32: Coating of Cores with a Mixture of Lipid and Hydrocolloid 600 g granulate prepared according to one of examples 27-30 were loaded into fluid bed device (Ventilus V-2.5/1, Innojet, Germany, equipped with an IPC3 product reservoir) and fluidised at a bed temperature of 20° C. at an air flow of 90 cubic meters/h. 135 g Dynasan® 116 and 15 g guar gum (Careguar, Caremoli, Germany) were heated on a hot plate (80° C.) equipped with a mechanical stirrer. The hot melt sprayed onto the granulate using a peristaltic pump and a top spraying procedure at a spray rate of 6.5 g/min. Samples of different amounts of coating were taken at time intervals, corresponding to 15 and 25% (w/w).

Example 33: Mucoadhesion Assay of Coated Granulate

Granulate prepared according to experiment 30 were coated according to experimental procedure 31 to different coating thickness and subjected to the mucoadhesion assay protocol described above, except that binding kinetics were followed up to 30 min.

Pork stomach binding of the granulate sample carrying 10% (w/w) coating was maximal after 6 min. Pork stomach binding of the granulate sample carrying 15% (w/w) coating was maximal after 9 min. Pork stomach binding of the granulate sample carrying 20% (w/w) coating was maximal after 12 min. Pork stomach binding of the granulate sample carrying 25% (w/w) coating was maximal after 25 min.

Example 34: Mucoadhesion Assay of Coated Granulate

Granulate prepared according to experiment 30 were coated according to experimental procedure 32 to different coating thickness and subjected to the mucoadhesion assay protocol described above, except that binding kinetics were followed up to 30 min.

Pork stomach binding of the granulate sample carrying 15% (w/w) coating was maximal after 14 min. Pork stomach binding of the granulate sample carrying 20% (w/w) coating was maximal after 25 min.

Example 35: Preparation of Granulate by Extrusion

A premix prepared according to the protocol of experiment 26, comprising 224 g palm stearin (Palmstearin 54, Juchem, Germany), 96 g alginate (Satialgine®, Cargill, France), 32 g pectin (Aglupectin® HS-RVP, Silvateam, Italy) and 32 g oat beta glucan (PromOat®, Tate & Lyle, Sweden), was fed via a volumetric dosing system (Dosimex DO-50, Gabler, Germany) into a powder inlet of a twin screw extruder (Extruder DE-40/10, Gabler, Germany, operating at 7 rpm) and extruded at a temperature range of 10-12° C. to strands of 1.5 mm diameter. Extruded strands were cut to granules of 0.8-2.5 mm length by means of rotating blades (running at 100 rpm). The premix was quantitatively converted into extrudate within less than 5 min.

Example 36: 10 kg Batch of Coated Granulate

A premix was prepared my melting 8.25 kg palm stearin (Palm Stearin 54, Bressmer, Germany) in a cooking pot over an induction plate. When the melt had a temperature of 60° C., 4.5 kg sodium alginate (Satialgine®, Cargill, France), 1.5 g oat fibre preparation (PromOat®, Tate&Lyle, Sweden), and 1.5 kg pectin (Pektin HV, Golden Peanut, Germany) were incorporated by means of a cooking spoon. The mixture was transferred in aliquots into zip-loc plastic bags and cooled to room temperature to form solid plates. Lipid-polymer plates were further cooled in a freezer set at −18° C. and then shredded to particles of ca. 5 mm and smaller by means of a blender (Vitamix®, Vita-Mix Corp., USA). The obtained premix was fed via a volumetric dosing system (Dosimex DO-50, Gabler, Germany) into a powder inlet of a twin screw extruder (Extruder DE-40/10, Gabler, Germany, operating at 10 rpm) and extruded at a temperature range of 10-12° C. to strands of 1.5 mm diameter. Extruded strands were cut to granules of 0.8-2.5 mm length by means of rotating blades (running at 100 rpm). The premix was quantitatively converted into extrudate within less than 5 min. The extrudate was transferred into plastic bags in aliquots of 990 g and stored at −18° C. To each bag, 9.9 g of PromOat® powder were added and thoroughly mixed with the extrudate. Subsequently, granules were optionally dried under vacuum at 25° C. and subjected to classification using a wire mesh sieves of 2 mm (mesh 10) and 1.0 mm (mesh 18). The classified granules were mixed and split into aliquots of 600 g. Aliquots were loaded into a fluid bed device (Ventilus V-2.5/1, Innojet, Germany, equipped with an IPC3 product reservoir) and fluidised at a bed temperature of 20° C. at an air flow of 80 cubic meters/h. 120 g Dynasan® 115 were molten in a beaker on a hot plate (at 90° C.) equipped with an overhead stirrer. The hot melt was quantitatively sprayed onto the granulate using a peristaltic pump and a top spraying procedure at a spray rate of 6.5 g/min. Aliquots were combined and a total of 10 kg of coated granulate was obtained and stored in a plastic container.

Example 37: Coated Granulate

Fourteen kg of a premix were prepared in seven batches of 2 kg each. For each batch, 0.9 kg palm stearin (Prifex® 300, Unimills, The Netherlands) and 0.1 kg linseed oil (manako BIO Leinöl human, Makana, Germany) were brought to a melt in a cooking pot over an induction plate. When the melt had a temperature of 60° C., 0.3 kg sodium alginate (Alginex®, Kimica, Japan), 0.1 kg oat fibre preparation (PromOat®, Tate&Lyle, Sweden) and 0.1 kg pectin (Aglupectin® HS-RVP, Silva, Italy) were incorporated by means of a cooking spoon. The mixture was transferred in aliquots into zip-loc plastic bags and cooled to room temperature to form solid plates. Lipid-polymer plates were further cooled in a freezer set at −18° C. and then shredded to particles of ca. 5 mm and smaller by means of a blender (Vitamix® Professional 750, Vita-Mix Corp., USA). The obtained premix was fed via a volumetric dosing system (Dosimex DO-50 Gabler, Germany) into a powder inlet of a twin screw extruder (Extruder DE-40/10, Gabler, Germany, operating at 10 rpm) and extruded at a temperature range of ca. 30° C. to strands of 1.0 mm diameter. Extruded strands were cut to granules of 0.8-2.5 mm length by means of rotating blades (running at 100 rpm). The extrudate was transferred into plastic bags in aliquots and stored at −18° C. Subsequently, granules were optionally dried under vacuum at 25° C. and subjected to classification using a wire mesh sieves (Atechnik, Germany) of 2 mm (mesh 10) and 1.0 mm (mesh 18). Material retained on the 2 mm sieve was subjected to comminution using a household blending device (MK55300, Siemens, Germany) and re-classified using the set of wire mesh sieves. Granules classified to a range of 1-2 mm were combined to give a yield of 9.0 kg and split into aliquots of 600 g. Batches (one aliquot per run, fifteen runs) were loaded into a fluid bed device (Ventilus V-2.5/1, Innojet, Germany, equipped with an IPC3 product reservoir) and fluidised at a bed temperature of 20° C. at an air flow of 65 m³/h. Per run, 120 kg palm stearin (Prifex® 300, Unimills, The Netherlands) were molten in a beaker on a hot plate (at 100° C.) equipped with an overhead stirrer. The hot melt was quantitatively sprayed onto the granulate using a peristaltic pump and a top spraying procedure at a spray rate of 6.5 g/min. Batches were combined, and a total of 10.67 kg of coated granulate was obtained and stored in a plastic container.

Example 38: Preparation of Tryptophan-Containing Granules

Granules was prepared by melting 2 g glycerol monolaurin (Mosselman, Belgium) and 2 g glycerol monoolein 40 (TCI, Belgium) at 55° C. L-Tryptophan (1 g, TCI, Belgium), hydroxypropyl methylcellulose (Metolose® 90SH-100000SR, Harke, Germany), and xanthan gum (0.5 g, Solegraells, Spain) were incorporated by mechanical mixing. The composition was transferred into a zip-loc-bag and cooled to −18° C. in a freezer. The material was first crushed by means of a hammer, shredded into a granulate using a kitchen blender (Bosch ProfiMIXX, Germany), optionally dried under vacuum at 25° C. and then classified through a set of wire mesh sieves (VWR International, Germany) to a granule size of below 1.0 mm and above 0.5 mm.

A sample of 200 mg of tryptophan-containing granules was suspended in 22 mL fasted-state simulated gastric fluid (FaSSGF) at 37° C. and agitated (shaker ST5 from CAT, Germany). FaSSGF was prepared by dissolving 1 g of NaCl (Sigma-Aldrich) in 450 mL of water, adding 30 mg of SIF powder (biorelvant.com), adjusting the pH to 2.0 with 0.1 N HCl (Sigma-Aldrich) and adding water to a final volume of 500 mL. Aliquots were removed from the supernatant at time intervals of 15 min, and the tryptophan concentration was determined by absorption measurement at a wavelength of 280 nm in a NanoDrop® 2000 device (Thermo Scientific, USA). Tryptophan release followed first-order kinetics with a half-time of 20 minutes.

A sample of 200 mg of tryptophan-containing granules was suspended in 22 mL fasted-state simulated intestinal fluid (FaSSIF) at 37° C. and agitated (shaker ST5 from CAT, Germany). FaSSIF was prepared by dissolving 0.21 g NaOH pellets (Sigma-Aldrich), 3.09 g of NaCl (Sigma-Aldrich) and 1.98 g sodium dihydrogen phosphate monohydrate (Sigma-Aldrich) in 450 mL of water, adding 1.12 g of SIF powder (biorelvant.com), adjusting the pH to 6.5 and adding water to a final volume of 500 mL. Aliquots were removed from the supernatant at time intervals of 15 min, and tryptophan concentration was determined by absorption measurement at a wavelength of 280 nm in a NanoDrop® 2000 device (Thermo Scientific, USA). Tryptophan release followed first-order kinetics with a half-time of 15 minutes.

Tryptophan Control 30 mg of tryptophan powder were suspended in 22 mL FaSSGF at 37° C. and agitated (shaker ST5 from CAT, Germany). Aliquots were removed at time intervals of 5 min, and tryptophan concentration was quantified using absorption measurement at a wavelength of 280 nm in a NanoDrop® 2000 device (Thermo Scientific, USA). Tryptophan was quantitatively dissolved after 10 minutes.

The invention claimed is:

1. An oral composition comprising an effective amount of
   (a) a first agent capable of inducing satiety, and
   (b) a second agent capable of augmenting the satiety-inducing effect of the first agent,
   wherein the first agent is a medium or long chain fatty acid compound, said fatty acid compound being comprised in a lipid component,
   wherein the second agent is a water-swellable or water-soluble polymeric component comprising at least one polymeric material selected from the group consisting of poly(carboxylates) and polysaccharides,
   wherein the weight ratio of the lipid component to the water-swellable or water-soluble polymeric component is in the range from 1 to 3,
   wherein the water swellable or water-soluble polymeric component is embedded within the lipid component in such a way that the water swellable or water-soluble polymeric component is dispersed within the lipid component, whether molecularly, colloidally or in the form of a solid suspension, and
   wherein the composition is free of a synthetic drug substance.

2. The composition of claim 1, wherein the first agent is a free or esterified medium or long chain fatty acid.

3. The composition of claim 2, wherein the free fatty acid is neutralized.

4. The composition of claim 1, wherein the water-swellable or water-soluble polymeric component comprises at least one polymeric material selected from the group consisting of poly(carboxylates), chitosan, cellulose ethers, and xanthan gum.

5. The composition of claim 4, wherein the polymeric material is at least partially crosslinked.

6. The composition of claim 4, wherein the poly(carboxylate) is selected from the group consisting of alginic acid, poly(acrylic acid), poly(methacrylic acid), copolymers of acrylic and methacrylic acid, and poly(hydroxyethyl methacrylic acid), and wherein the cellulose ether is selected from the group consisting of hydroxyethyl cellulose, hydroxypropyl cellulose, hydroxypropyl methylcellulose, methylcellulose, and carboxymethylcellulose.

7. The composition of claim 6, wherein the poly(carboxylate) and/or the carboxymethylcellulose is at least partially neutralized.

8. The composition of claim 1, further comprising an amino acid, a vitamin, and/or a micro-nutrient.

9. The composition of claim 1, wherein the lipid component forms a continuous phase in which the water-swellable or water-soluble polymeric component is discontinuous and in dispersed form.

10. The composition of claim 1, wherein the water-swellable or water-soluble polymeric component comprises a mucoadhesive polymer.

11. The composition of claim 1, wherein the water-swellable or water-soluble polymeric component is a hydrophilic or an amphiphilic polymer of a solubility in water of at least 1 mg/L.

12. The composition of claim 1, wherein the first agent is a free fatty acid, a salt of a fatty acid, or an esterified fatty acid, and wherein the esterified fatty acid is a monoglyceride, diglyceride or triglyceride.

13. A method of inducing satiety in a subject, said method comprising a step of orally administering the composition of claim 1.

14. The method of claim 13, wherein the subject is a human subject having developed overweight or obesity.

15. The method of claim 13, wherein the oral administration of the composition is performed at least once a day over a period of at least one week.

16. The method of claim 13, further comprising the step of monitoring a subject's adherence to, or the effectiveness of, a predefined therapeutic regimen of orally administering the composition with a programmed electronic device.

17. A method of treating overweight or obesity in a subject, said method comprising a step of orally administering the composition of claim 1.

18. A method of controlling or reducing the body weight of a subject, said method comprising a step of orally administering the composition of claim 1.

19. A body weight management system comprising the composition of claim 1 and a programmed electronic device configured for the collection, storage and/or display of information relating to a subject's adherence, or the effectiveness of, a predefined therapeutic regimen of orally administering the composition.

* * * * *